United States Patent
Vierlinger et al.

(10) Patent No.: US 10,100,364 B2
(45) Date of Patent: Oct. 16, 2018

(54) SET OF TUMOR-MARKERS

(71) Applicant: AIT AUSTRIAN INSTITUTE OF TECHNOLOGY GMBH, Vienna (AT)

(72) Inventors: Klemens Vierlinger, Vienna (AT); Martin Lauss, Altenfelden (AT); Albert Kriegner, Vienna (AT); Christa Noehammer, Vienna (AT)

(73) Assignee: AIT AUSTRIAN INSTITUTE OF TECHNOLOGY GMBH, Vienna (AT)

( * ) Notice: Subject to any disclaimer, the term of this patent is extended or adjusted under 35 U.S.C. 154(b) by 121 days.

(21) Appl. No.: 14/691,405

(22) Filed: Apr. 20, 2015

(65) Prior Publication Data

US 2015/0252437 A1   Sep. 10, 2015

Related U.S. Application Data

(63) Continuation of application No. 12/675,736, filed as application No. PCT/AT2008/000311 on Aug. 29, 2008.

(30) Foreign Application Priority Data

Aug. 30, 2007 (AT) .................. A 1359/2007

(51) Int. Cl.
```
C07H 21/04       (2006.01)
C12Q 1/6886      (2018.01)
G01N 33/574      (2006.01)
G06F 19/20       (2011.01)
G06F 19/24       (2011.01)
```
(52) U.S. Cl.
CPC ..... *C12Q 1/6886* (2013.01); *G01N 33/57484* (2013.01); *G06F 19/20* (2013.01); *C12Q 2600/118* (2013.01); *C12Q 2600/158* (2013.01); *C12Q 2600/16* (2013.01); *G01N 2800/60* (2013.01); *G06F 19/24* (2013.01)

(58) Field of Classification Search
None
See application file for complete search history.

(56) References Cited

U.S. PATENT DOCUMENTS

2001/0051344 A1   12/2001  Shalon et al. .................. 435/6

OTHER PUBLICATIONS

Benito et al., "Adjustment of systematic microarray data biases," Bioinformatics, 20:105-14, 2004.
Bolstad et al., "A comparison of normalization methods for high density oligonucleotide array data based on variance and bias," Bioinformatics, 19:185-93, 2003.
Chen et al., Molecular and Cellular Proteomics 1:304-313, 2002.
Eszlinger et al., "Meta- and reanalysis of gene expression profiles of hot and cold thyroid nodules and papillary thyroid carcinoma for gene groups," Clin. Endocrinol. Metab., 91:1934-1942, 2006.
Griffith et al., "Meta-analysis and meta-review of thyroid cancer gene expression profiling studies identifies important diagnostic biomarkers," J. Clin. Oncol., 24:5043-51, 2006.
He et al., "The role of microRNA genes in papillary thyroid carcinoma," Proc. Natl. Acad. Sci. USA, 102:19075-80, 2005.
Huang et al., "Gene expression in papillary thyroid carcinoma reveals highly consistent profiles," Proc. Natl. Acad. Sci. USA, 98:15044-9, 2001.
Jarzab et al., "Gene expression profile of papillary thyroid cancer: sources of variability and diagnostic implications," Cancer Res., 65:1587-97, 2005.
Kroese et al, Genetics in Medicine 6(6) :475-480, 2004.
Lacroix et al., "Follicular thyroid tumors with the PAX8-PPARgammal rearrangement display characteristic genetic alterations," Am. J. Pathol., 167:223-31, 2005.
Lucentini, (The Scientist, 18(24):20, 2004), teaches that it strikingly common for follow-up studies to find gene-disease associations wrong.
Mullis et al., "Agreement in Breast Cancer Classification between Microarray and Quantitative Reverse Transcription PCR from Fresh-Frozen and Formalin-Fixed, Paraffin-Embedded Tissues", Clinical Chemistry, 53(7):1273-1279, 2007.
Nindl et al., "Identification of differentially expressed genes in cutaneous squamous cell carcinoma by microarray expression profiling", Molecular Cancer, 5(30):1-17, 2006.
Shen et al., "Eigengene-based linear discriminant model for tumor classification using gene expression microarray data," Bioinformatics, 22:2635-42, 2006.
Smyth and Speed, "Normalization of cDNA microarray data," Methods, 31:265-73, 2003.
Tibshirani et al., "Diagnosis of multiple cancer types by shrunken centroids of gene expression," Proc. Natl. Acad. Sci. USA, 99:105-14, 2002.
Wang and Zhu, "Improved centroids estimation for the nearest shrunken centroid classifier," Bioinformatics, 23:972-9, 2007.
Weber et al., "Genetic classification of benign and malignant thyroid follicular neoplasia based on a three-gene combination," J. Clin. Endocrinol. Metab., 90:2512-21, 2005.
Wu, J. Pathol. 195(1):53-65, 2001.

*Primary Examiner* — Celine X Qian
(74) *Attorney, Agent, or Firm* — Norton Rose Fulbright US LLP

(57) ABSTRACT

The present invention provides a set of moieties specific for tumor markers, in particular of follicular thyroid carcinoma (FTC) and papillary thyroid carcinoma (PTC) as well as a method for identifying markers of any genetic disease.

10 Claims, 5 Drawing Sheets

SET OF TUMOR-MARKERS

CROSS-REFERENCE TO RELATED APPLICATIONS

This application is a continuation of U.S. patent application Ser. No. 12/675,736, which is a national phase application under 35 U.S.C. § 371 of International Application No. PCT/AT2008/000311 filed 29 Aug. 2008, which claims priority to Austrian Application No. A 1359/2007 filed 30 Aug. 2007. The entire text of each of the above-referenced disclosures is specifically incorporated herein by reference without disclaimer.

BACKGROUND OF THE INVENTION

1. Field of the Invention

The present invention relates to the field of cancer diagnosis and diagnostic means therefor.

2. Description of Related Art

Thyroid nodules are endemic in iodine deficient areas, like Europe's alpine regions, where they have a prevalence of 10-20%. They are classified by their histology into the 2 benign types Struma nodosa (SN) and Follicular Thyroid Adenoma (FTA) and the malignant entities Follicular Thyroid Carcinoma (FTC), Papillary Thyroid Carcinoma (PTC), Medullary Thyroid Carcinoma (MTC) and Anaplastic Thyroid Carcinoma (ATC). Conventionally, discrimination between benign and malignant thyroid nodules is done by scintigraphy and fine needle aspiration followed by histology. Despite many advances in the diagnosis and therapy of thyroid nodules and thyroid cancer, these methods have a well-known lack of specificity, particularly for the discrimination between FTA and FTC, which leads to a number of patients unnecessarily treated for malignant disease.

Given the diagnostic limitations of previous methods, in particular fine needle aspiration followed by cytology, multiple investigators have carried out expression profiling studies with hopes of identifying new diagnostic tools. Such analyses attempt to identify differentially expressed genes with an important role in disease development or progression using large-scale transcript-level expression profiling technologies such as cDNA microarrays, oligonucleotide arrays and Serial Analysis of Gene Expression (SAGE). Typically, dozens or hundreds of genes are identified, many of which are expected to be false positives, and only a small fraction useful as diagnostic/prognostic markers or therapeutic targets (Griffith et al., J Clin Oncol 24(31):5043-5051 (2006)).

In other types of cancer it has been shown that gene expression profiling can add substantial value to the discrimination of the different clinically relevant tumour-entities. The US 2006/183141 A e.g. describes classification of tumor markers from a core serum response signature. Different studies have tried to classify the different entities of thyroid carcinoma on the basis of their gene expression profiles each of them discriminates between 2 of the 5 entities. However, the studies have no or very few genes in common and applying a classier from one study to the data from another study generally yields poor classification results.

SUMMARY OF THE INVENTION

It is a goal of the present invention to provide reliable distinctive markers for the diagnosis of cancer, in particular to distinguish benign thyroid nodules from malignant follicular thyroid carcinoma (FTC) and papillary thyroid carcinoma (PTC).

Therefore the present invention provides a set of moieties specific for at least 3 tumor markers selected from the tumor markers PI-1 to PI-33, PII-1 to PII-64, PIII-1 to PIII-70, fi-1 to fi-147, PIV-1 to PIV-9, preferably PIV-4 or PIV-5, and PV-1 to PV-11, preferably PV-1, PV-2 and PV-4 to PV-11. These tumor markers are related to different genes aberrantly expressed in tumors and are given in tables 1 to 6 and can be identified by their gene identification sign, their descriptive gene name, but most unambiguously by their UniGeneID or their Accession number referring to specific sequences in common sequence databases such as NCBI GenBank, EMBL-EBI Database, EnsEMBL or the DNA Data Bank of Japan. These markers have been identified in form of preferred sets (PI to PV, FI) but can be combined in any form as targets for the inventive set.

TABLE 1

PTC marker set PI-1 to PI-33

| Number marker P I- | gene | description of gene | Accession Nr. | UniGeneID |
|---|---|---|---|---|
| 1 | BBS9 | Bardet-Biedl syndrome 9 | NM_198428 NM_001033605 NM_001033604 NM_014451 | Hs.372360 |
| 2 | C13orf1 | Chromosome 13 open reading frame 1 | NM_020456 | Hs.44235 |
| 3 | CBFA2T3 | Core-binding factor, runt domain, alpha subunit 2 | NM_005187 NM_175931 | Hs.513811 |
| 4 | CDT1 | Chromatin licensing and DANN replication factor 1 | NM_030928 | Hs.122908 |
| 5 | CRK | V-crk sarcoma virus CT10 oncogene homolog (avian) | NM_016823 NM_005206 | Hs.638121 |
| 6 | CTPS | CTP synthase | NM_001905 | Hs.473087 |
| 7 | DAPK2 | Death-associated protein kinase 2 | NM_014326 | Hs.237886 |
| 8 | EIF5 | Eukaryotic translation initiation factor 5 | NM_001969 NM_183004 | Hs.433702 |
| 9 | EREG | Epiregulin | NM_001432 | Hs.115263 |
| 10 | GK | Glycerol kinase | NM_203391 NM_000167 | Hs.1466 |
| 11 | GPATCH8 | G patch domain containing 8 | NM_001002909 | Hs.463129 |
| 12 | HDGF | Hepatoma-derived growth factor (high-mobility group protein 1-like) | NM_004494 | Hs.506748 |

TABLE 1-continued

PTC marker set PI-1 to PI-33

| Number P I- | marker gene | description of gene | Accession Nr. | UniGeneID |
|---|---|---|---|---|
| 13 | IRF2BP1 | Interferon regulatory factor 2 binding protein 1 | NM_015649 | Hs.515477 |
| 14 | KRT83 | Keratin 83 | NM_002282 | Hs.661428 |
| 15 | MYOD1 | Myogenic differentiation 1 | NM_002478 | Hs.181768 |
| 16 | NME6 | Non-metastatic cells 6, protein expressed in (nucleoside-diphosphate kinase) | NM_005793 | Hs.465558 |
| 17 | POLE3 | Polymerase (DNA directed), epsilon 3 (p17 subunit) | NM_017443 | Hs.108112 |
| 18 | PPP1R13B | Protein phosphatase 1, regulatory (inhibitor) subunit 13B | NM_015316 | Hs.436113 |
| 19 | PRPH2 | Peripherin 2 (retinal degeneration, slow) | NM_000322 | Hs.654489 |
| 20 | RASSF7 | Ras association (RalGDS/AF-6) domain family 7 | NM_003475 | Hs.72925 |
| 21 | ROCK2 | Rho-associated, coiled-coil containing protein kinase 2 | NM_004850 | Hs.591600 |
| 22 | RTN1 | Reticulon 1 | NM_021136 NM_206857 NM_206852 | Hs.368626 |
| 23 | S100B | S100 calcium binding protein B | NM_006272 | Hs.422181 |
| 24 | SLIT2 | Slit homolog 2 (*Drosophila*) | NM_004787 | Hs.29802 |
| 25 | SNRPB2 | Small nuclear ribonucleoprotein polypeptide B" | NM_003092 NM_198220 | Hs.280378 |
| 26 | SPAG7 | Sperm associated antigen 7 | NM_004890 | Hs.90436 |
| 27 | STAU1 | Staufen, RNA binding protein, homolog 1 (*Drosophila*) | NM_017453 NM_001037328 NM_004602 NM_017452 NM_017454 | Hs.596704 |
| 28 | SUPT5H | Suppressor of Ty 5 homolog (*S. cerevisiae*) | NM_003169 | Hs.631604 |
| 29 | TBX10 | T-box 10 | NM_005995 | Hs.454480 |
| 30 | TLK1 | Tousled-like kinase 1 | NM_012290 | Hs.655640 |
| 31 | TM4SF4 | Transmembrane 4 L six family member 4 | NM_004617 | Hs.133527 |
| 32 | TXN | Thioredoxin | NM_003329 | Hs.435136 |
| 33 | UFD1L | Ubiquitin fusion degradation 1 like (yeast) | NM_005659 NM_001035247 | Hs.474213 |

TABLE 2

PTC marker set PII-1 to PII-64

| Number P II- | marker gene | description of gene | Accession Nr. | UniGeneID |
|---|---|---|---|---|
| 1 | ADH1B | Alcohol dehydrogenase IB (class I), beta polypeptide | NM_000668 | Hs.4 |
| 2 | AGR2 | Anterior gradient homolog 2 (*Xenopus laevis*) | NM_006408 | Hs.530009 |
| 3 | AGTR1 | Angiotensin II receptor, type 1 | NM_031850 NM_004835 NM_009585 NM_032049 | Hs.477887 |
| 4 | AGTR1 | Angiotensin II receptor, type 1 | NM_000685 | Hs.654382 |
| 5 | ALDH1A1 | Aldehyde dehydrogenase 1 family, member A1 | NM_000689 | Hs.76392 |
| 6 | ALDH1A3 | Aldehyde dehydrogenase 1 family, member A3 | NM_000693 | Hs.459538 |
| 7 | AMIGO2 | Adhesion molecule with Ig-like domain 2 | NM_181847 | Hs.121520 |
| 8 | ATP2C2 | ATPase, Ca++ transporting, type 2C, member 2 | NM_014861 | Hs.6168 |
| 9 | BID | BH3 interacting domain death agonist | NM_197966 NM_001196 NM_197967 | Hs.591054 |
| 10 | C7orf24 | Chromosome 7 open reading frame 24 | NM_024051 | Hs.530024 |
| 11 | CA4 | Carbonic anhydrase IV | NM_000717 | Hs.89485 |
| 12 | CCL21 | Chemokine (C-C motif) ligand 21 | NM_002989 | Hs.57907 |
| 13 | CD55 | CD55 molecule, decay accelerating factor for complement (Cromer blood group) | NM_000574 | Hs.527653 |
| 14 | CDH16 | Cadherin 16, KSP-cadherin | NM_004062 | Hs.513660 |
| 15 | CDH3 | Cadherin 3, type 1, P-cadherin (placental) | NM_133458 NM_001793 | Hs.461074 |
| 16 | CFI | Complement factor I | NM_000204 | Hs.312485 |
| 17 | CHI3L1 | Chitinase 3-like 1 (cartilage glycoprotein-39) | NM_001276 | Hs.382202 |
| 18 | CHST2 | Carbohydrate (N-acetylglucosamine-6-O) sulfotransferase 2 | NM_004267 | Hs.8786 |

TABLE 2-continued

PTC marker set PII-1 to PII-64

| Number P II- | marker gene | description of gene | Accession Nr. | UniGeneID |
|---|---|---|---|---|
| 19 | CITED2 | Cbp/p300-interacting transactivator, with Glu/Asp-rich carboxy-terminal domain, 2 | NM_006079 | Hs.82071 |
| 20 | CLCNKB | Chloride channel Kb | NM_000085 | Hs.352243 |
| 21 | COMP | Cartilage oligomeric matrix protein | NM_000095 | Hs.1584 |
| 22 | CTSH | Cathepsin H | NM_004390 NM_148979 | Hs.148641 |
| 23 | DIO2 | Deiodinase, iodothyronine, type II | NM_013989 NM_000793 NM_001007023 | Hs.202354 |
| 24 | DIRAS3 | DIRAS family, GTP-binding RAS-like 3 | NM_004675 | Hs.194695 |
| 25 | DUSP4 | Dual specificity phosphatase 4 | NM_057158 NM_001394 | Hs.417962 |
| 26 | DUSP5 | Dual specificity phosphatase 5 | NM_004419 | Hs.2128 |
| 27 | EDN3 | Endothelin 3 | NM_207032 NM_207034 NM_207033 NM_000114 | Hs.1408 |
| 28 | ENTPD1 | Ectonucleoside triphosphate diphosphohydrolase 1 | NM_001776 NM_001098175 | Hs.576612 |
| 29 | FHL1 | Four and a half LIM domains 1 | NM_001449 | Hs.435369 |
| 30 | GDF15 | Growth differentiation factor 15 | NM_004864 | Hs.616962 |
| 31 | GPM6A | Glycoprotein M6A | NM_201591 NM_005277 NM_201592 | Hs.75819 |
| 32 | HBA1 | Hemoglobin, alpha 1 | NM_000558 | Hs.449630 |
| 33 | IRS1 | Insulin receptor substrate 1 | NM_005544 | Hs.471508 |
| 34 | KCNJ2 | Potassium inwardly-rectifying channel, subfamily J, member 2 | NM_000891 | Hs.1547 |
| 35 | KCNN4 | Potassium intermediate/small conductance calcium-activated channel, subfamily N, member 4 | NM_002250 | Hs.10082 |
| 36 | KLK10 | Kallikrein-related peptidase 10 | NM_002776 NM_001077500 NM_145888 | Hs.275464 |
| 37 | LAMB3 | Laminin, beta 3 | NM_001017402 NM_000228 | Hs.497636 |
| 38 | LCN2 | Lipocalin 2 (oncogene 24p3) | NM_005564 | Hs.204238 |
| 39 | LMOD1 | Leiomodin 1 (smooth muscle) | NM_012134 | Hs.519075 |
| 40 | MATN2 | Matrilin 2 | NM_002380 NM_030583 | Hs.189445 |
| 41 | MPPED2 | Metallophosphoesterase domain containing 2 | NM_001584 | Hs.289795 |
| 42 | MVP | Major vault protein | NM_017458 NM_005115 | Hs.632177 |
| 43 | NELL2 | NEL-like 2 (chicken) | NM_006159 | Hs.505326 |
| 44 | NFE2L3 | Nuclear factor (erythroid-derived 2)-like 3 | NM_004289 | Hs.404741 |
| 45 | NPC2 | Niemann-Pick disease, type C2 | NM_006432 | Hs.433222 |
| 46 | NRCAM | Neuronal cell adhesion molecule | NM_001037132 NM_005010 NM_001037133 | Hs.21422 |
| 47 | NRIP1 | Nuclear receptor interacting protein 1 | NM_003489 | Hs.155017 |
| 48 | PAPSS2 | 3'-phosphoadenosine 5'-phosphosulfate synthase 2 | NM_001015880 NM_004670 | Hs.524491 |
| 49 | PDLIM4 | PDZ and LIM domain 4 | NM_003687 | Hs.424312 |
| 50 | PDZK1IP1 | PDZK1 interacting protein 1 | NM_005764 | Hs.431099 |
| 51 | PIP3-E | Phosphoinositide-binding protein PIP3-E | NM_015553 | Hs.146100 |
| 52 | PLAU | Plasminogen activator, urokinase | NM_002658 | Hs.77274 |
| 53 | PRSS2 | Protease, serine, 2 (trypsin 2) | NM_002770 | Hs.622865 |
| 54 | PRSS23 | Protease, serine, 23 | NM_007173 | Hs.25338 |
| 55 | RAP1GAP | RAP1 GTPase activating protein | NM_002885 | Hs.148178 |
| 56 | S100A11 | S100 calcium binding protein A11 | NM_005620 | Hs.417004 |
| 57 | SFTPB | Surfactant, pulmonary-associated protein B | NM_198843 NM_000542 | Hs.512690 |
| 58 | SLPI | Secretory leukocyte peptidase inhibitor | NM_003064 | Hs.517070 |
| 59 | SOD3 | Superoxide dismutase 3, extracellular | NM_003102 | Hs.2420 |
| 60 | SPINT1 | Serine peptidase inhibitor, Kunitz type 1 | NM_181642 NM_003710 NM_001032367 | Hs.233950 |
| 61 | SYNE1 | Spectrin repeat containing, nuclear envelope 1 | NM_182961 NM_033071 NM_015293 NM_133650 | Hs.12967 |
| 62 | TACSTD2 | Tumor-associated calcium signal transducer 2 | NM_002353 | Hs.23582 |
| 63 | UPP1 | Uridine phosphorylase 1 | NM_181597 NM_003364 | Hs.488240 |
| 64 | WASF3 | WAS protein family, member 3 | NM_006646 | Hs.635221 |

TABLE 3

PTC marker set PIII-1 to PIII-70

| Number P III- | marker gene | description of gene | Accession Nr. | UniGeneID |
|---|---|---|---|---|
| 1 | APOE | Apolipoprotein E | NM_000041 | Hs.654439 |
| 2 | ATIC | 5-aminoimidazole-4-carboxamide ribonucleotide formyltransferase/IMP cyclohydrolase | NM_004044 | Hs.90280 |
| 3 | BASP1 | Brain abundant, membrane attached signal protein 1 | NM_006317 | Hs.201641 |
| 4 | C9orf61 | Chromosome 9 open reading frame 61 | NM_004816 | Hs.118003 |
| 5 | CCL13 | Chemokine (C-C motif) ligand 13 | NM_005408 | Hs.414629 |
| 6 | CD36 | CD36 molecule (thrombospondin receptor) | NM_001001548 NM_001001547 NM_000072 | Hs.120949 |
| 7 | CDH6 | Cadherin 6, type 2, K-cadherin (fetal kidney) | NM_004932 | Hs.171054 |
| 8 | CFB | Complement factor B | NM_001710 | Hs.69771 |
| 9 | CFD | Complement factor D (adipsin) | NM_001928 | Hs.155597 |
| 10 | CLDN10 | Claudin 10 | NM_182848 NM_006984 | Hs.534377 |
| 11 | COL11A1 | Collagen, type XI, alpha 1 | NM_080629 NM_001854 NM_080630 | Hs.523446 |
| 12 | COL13A1 | Collagen, type XIII, alpha 1 | NM_005203 NM_080804 NM_080798 NM_080803 NM_080802 NM_080799 NM_080800 NM_080801 NM_080808 NM_080809 NM_080805 NM_080807 NM_080806 NM_080811 NM_080810 NM_080812 NM_080813 NM_080814 NM_080815 | Hs.211933 |
| 13 | CORO2B | Coronin, actin binding protein, 2B | NM_006091 | Hs.551213 |
| 14 | CRLF1 | Cytokine receptor-like factor 1 | NM_004750 | Hs.114948 |
| 15 | CXorf6 | Chromosome X open reading frame 6 | NM_005491 | Hs.20136 |
| 16 | DDB2 | Damage-specific DNA binding protein 2, 48 kDa | NM_000107 | Hs.655280 |
| 17 | DPP6 | Dipeptidyl-peptidase 6 | NM_001039350 NM_130797 NM_001936 | Hs.490684 |
| 18 | ECM1 | Extracellular matrix protein 1 | NM_004425 NM_022664 | Hs.81071 |
| 19 | EFEMP1 | EGF-containing fibulin-like extracellular matrix protein 1 | NM_004105 NM_001039348 NM_001039349 | Hs.76224 |
| 20 | ESRRG | Estrogen-related receptor gamma | NM_206594 NM_001438 NM_206595 | Hs.444225 |
| 21 | ETHE1 | Ethylmalonic encephalopathy 1 | NM_014297 | Hs.7486 |
| 22 | FAS | Fas (TNF receptor superfamily, member 6) | NM_000043 NM_152872 NM_152871 NM_152873 NM_152875 NM_152874 NM_152877 NM_152876 | Hs.244139 |
| 23 | FMOD | Fibromodulin | NM_002023 | Hs.519168 |
| 24 | GABBR2 | Gamma-aminobutyric acid (GABA) B receptor, 2 | NM_005458 | Hs.198612 |
| 25 | GALE | UDP-galactose-4-epimerase | NM_000403 NM_001008216 | Hs.632380 |
| 26 | GATM | Glycine amidinotransferase (L-arginine: glycine amidinotransferase) | NM_001482 | Hs.75335 |
| 27 | GDF10 | Growth differentiation factor 10 | NM_004962 | Hs.2171 |
| 28 | GHR | Growth hormone receptor | NM_000163 | Hs.125180 |
| 29 | GPC3 | Glypican 3 | NM_004484 | Hs.644108 |
| 30 | ICAM1 | Intercellular adhesion molecule 1 (CD54), human rhinovirus receptor | NM_000201 | Hs.643447 |
| 31 | ID3 | Inhibitor of DNA binding 3, dominant negative helix-loop-helix protein | NM_002167 | Hs.76884 |
| 32 | IER2 | Immediate early response 2 | NM_004907 | Hs.501629 |
| 33 | IGFBP6 | Insulin-like growth factor binding protein 6 | NM_002178 | Hs.274313 |
| 34 | IQGAP2 | IQ motif containing GTPase activating protein 2 | NM_006633 | Hs.291030 |
| 35 | ITGA2 | Integrin, alpha 2 (CD49B, alpha 2 subunit of VLA-2 receptor) | NM_002203 | Hs.482077 |
| 36 | ITGA3 | Integrin, alpha 3 (antigen CD49C, alpha 3 subunit of VLA-3 receptor) | NM_002204 NM_005501 | Hs.265829 |
| 37 | ITM2A | Integral membrane protein 2A | NM_004867 | Hs.17109 |
| 38 | KIAA0746 | KIAA0746 protein | NM_015187 | Hs.479384 |
| 39 | LRIG1 | Leucine-rich repeats and immunoglobulin-like domains 1 | NM_015541 | Hs.518055 |
| 40 | LRP2 | Low density lipoprotein-related protein 2 | NM_004525 | Hs.470538 |
| 41 | LY6E | Lymphocyte antigen 6 complex, locus E | NM_002346 | Hs.521903 |

TABLE 3-continued

PTC marker set PIII-1 to PIII-70

| Number P III- | marker gene | description of gene | Accession Nr. | UniGeneID |
|---|---|---|---|---|
| 42 | MAPK13 | Mitogen-activated protein kinase 13 | NM_002754 | Hs.178695 |
| 43 | MDK | Midkine (neurite growth-promoting factor 2) | NM_001012334 NM_001012333 NM_002391 | Hs.82045 |
| 44 | MLLT11 | Myeloid/lymphoid or mixed-lineage leukemia (trithorax homolog, Drosophila) | NM_006818 | Hs.75823 |
| 45 | MMRN1 | Multimerin 1 | NM_007351 | Hs.268107 |
| 46 | MTMR11 | Myotubularin related protein 11 | NM_181873 | Hs.425144 |
| 47 | MXRA8 | Matrix-remodelling associated 8 | NM_032348 | Hs.558570 |
| 48 | NAB2 | NGFI-A binding protein 2 (EGR1 binding protein 2) | NM_005967 | Hs.159223 |
| 49 | NMU | Neuromedin U | NM_006681 | Hs.418367 |
| 50 | OCA2 | Oculocutaneous albinism II (pink-eye dilution homolog, mouse) | NM_000275 | Hs.654411 |
| 51 | PDE5A | Phosphodiesterase 5A, cGMP-specific | NM_001083 NM_033430 NM_033437 | Hs.647971 |
| 52 | PLAG1 | Pleiomorphic adenoma gene 1 | NM_002655 | Hs.14968 |
| 53 | PLP2 | Proteolipid protein 2 (colonic epithelium-enriched) | NM_002668 | Hs.77422 |
| 54 | PLXNC1 | Plexin C1 | NM_005761 | Hs.584845 |
| 55 | PRKCQ | Protein kinase C, theta | NM_006257 | Hs.498570 |
| 56 | PRUNE | Prune homolog (Drosophila) | NM_021222 | Hs.78524 |
| 57 | RAB27A | RAB27A, member RAS oncogene family | NM_004580 NM_183234 NM_183235 NM_183236 | Hs.654978 |
| 58 | RYR2 | Ryanodine receptor 2 (cardiac) | NM_001035 | Hs.109514 |
| 59 | SCEL | Sciellin | NM_144777 NM_003843 | Hs.534699 |
| 60 | SELENBP1 | Selenium binding protein 1 | NM_003944 | Hs.632460 |
| 61 | SORBS2 | Sorbin and SH3 domain containing 2 | NM_021069 NM_003603 | Hs.655143 |
| 62 | STMN2 | Stathmin-like 2 | NM_007029 | Hs.521651 |
| 63 | TBC1D4 | TBC1 domain family, member 4 | NM_014832 | Hs.210891 |
| 64 | TM4SF4 | Transmembrane 4 L six family member 4 | NM_004617 | Hs.133527 |
| 65 | TNC | Tenascin C (hexabrachion) | NM_002160 | Hs.143250 |
| 66 | TPD52L1 | Tumor protein D52-like 1 | NM_001003395 NM_003287 NM_001003396 NM_001003397 | Hs.591347 |
| 67 | TSC22D1 | TSC22 domain family, member 1 | NM_183422 NM_006022 | Hs.507916 |
| 68 | TTC30A | Tetratricopeptide repeat domain 30A | NM_152275 | Hs.128384 |
| 69 | VLDLR | Very low density lipoprotein receptor | NM_003383 NM_001018056 | Hs.370422 |
| 70 | WFS1 | Wolfram syndrome 1 (wolframin) | NM_006005 | Hs.518602 |

TABLE 4

FTC marker set FI-1 to FI-147

| Number FI- | marker gene | description of gene | Accession Nr. | UniGeneID |
|---|---|---|---|---|
| 1 | AATF | Apoptosis antagonizing transcription factor | NM_012138 | Hs.195740 |
| 2 | ACOX3 | Acyl-Coenzyme A oxidase 3, pristanoyl | NM_003501 | Hs.479122 |
| 3 | AHDC1 | AT hook, DNA binding motif, containing 1 | NM_001029882 | Hs.469280 |
| 4 | ALAS2 | Aminolevulinate, delta-, synthase 2 (sideroblastic/hypochromic anemia) | NM_000032 NM_001037968 NM_001037967 NM_001037969 | Hs.522666 |
| 5 | ALKBH1 | AlkB, alkylation repair homolog 1 (E. coli) | NM_006020 | Hs.94542 |
| 6 | ANGPTL2 | Angiopoietin-like 2 | NM_012098 | Hs.653262 |
| 7 | AP2A2 | Adaptor-related protein complex 2, alpha 2 subunit | NM_012305 | Hs.19121 |
| 8 | APOBEC3G | Apolipoprotein B mRNA editing enzyme, catalytic polypeptide-like 3G | NM_021822 | Hs.660143 |
| 9 | APRIN | Androgen-induced proliferation inhibitor | NM_015032 | Hs.693663 |
| 10 | ARNT | Aryl hydrocarbon receptor nuclear translocator | NM_001668 NM_178427 NM_178426 | Hs.632446 |
| 11 | AZGP1 | Alpha-2-glycoprotein 1, zinc-binding | NM_001185 | Hs.546239 |

TABLE 4-continued

FTC marker set FI-1 to FI-147

| Number FI- | marker gene | description of gene | Accession Nr. | UniGeneID |
|---|---|---|---|---|
| 12 | BAT2D1 | BAT2 domain containing 1 | NM_015172 | Hs.494614 |
| 13 | BATF | Basic leucine zipper transcription factor, ATF-like | NM_006399 | Hs.509964 |
| 14 | BPHL | Biphenyl hydrolase-like (serine hydrolase) | NM_004332 | Hs.10136 |
| 15 | C13orf1 | Chromosome 13 open reading frame 1 | NM_020456 | Hs.44235 |
| 16 | C14orf1 | Chromosome 14 open reading frame 1 | NM_007176 | Hs.15106 |
| 17 | C2orf3 | Chromosome 2 open reading frame 3 | NM_003203 | Hs.303808 |
| 18 | CBFB | Core-binding factor, beta subunit | NM_001755 NM_022845 | Hs.460988 |
| 19 | CBR3 | Carbonyl reductase 3 | NM_001236 | Hs.154510 |
| 20 | CBX5 | Chromobox homolog 5 (HP1 alpha homolog, Drosophila) | NM_012117 | Hs.632724 |
| 21 | CCNE2 | Cyclin E2 | NM_057749 NM_057735 | Hs.567387 |
| 22 | CD46 | CD46 molecule, complement regulatory protein | NM_002389 NM_172354 NM_172351 NM_172355 NM_172352 NM_172359 NM_172357 NM_172360 NM_153826 NM_172358 NM_172356 NM_172353 NM_172361 NM_172350 | Hs.510402 |
| 23 | CHPF | Chondroitin polymerizing factor | NM_024536 | Hs.516711 |
| 24 | CHST3 | Carbohydrate (chondroitin 6) sulfotransferase 3 | NM_004273 | Hs.158304 |
| 25 | CLCN2 | Chloride channel 2 | NM_004366 | Hs.436847 |
| 26 | CLCN4 | Chloride channel 4 | NM_001830 | Hs.495674 |
| 27 | CLIC5 | Chloride intracellular channel 5 | NM_016929 | Hs.485489 |
| 28 | CNOT2 | CCR4-NOT transcription complex, subunit 2 | NM_014515 | Hs.133350 |
| 29 | COPS6 | COP9 constitutive photomorphogenic homolog subunit 6 (Arabidopsis) | NM_006833 | Hs.15591 |
| 30 | CPZ | Carboxypeptidase Z | NM_001014448 NM_001014447 NM_003652 | Hs.78068 |
| 31 | CSK | C-src tyrosine kinase | NM_004383 | Hs.77793 |
| 32 | CTDP1 | CTD (carboxy-terminal domain, RNA polymerase II, polypeptide A) phosphatase, subunit 1 | NM_004715 NM_048368 | Hs.465490 |
| 33 | DDEF2 | Development and differentiation enhancing factor 2 | NM_003887 | Hs.555902 |
| 34 | DKFZP586H2123 | Regeneration associated muscle protease | NM_015430 NM_001001991 | Hs.55044 |
| 35 | DLG2 | Discs, large homolog 2, chapsyn-110 (Drosophila) | NM_001364 | Hs.654862 |
| 36 | DPAGT1 | Dolichyl-phosphate (UDP-N-acetylglucosamine) N-acetylglucosaminephosphotransferase 1 (GlcNAc-1-P transferase) | NM_001382 NM_203316 | Hs.524081 |
| 37 | DSCR1 | Down syndrome critical region gene 1 | NM_004414 NM_203418 NM_203417 | Hs.282326 |
| 38 | DUSP8 | Dual specificity phosphatase 8 | NM_004420 | Hs.41688 |
| 39 | EI24 | Etoposide induced 2.4 mRNA | NM_004879 NM_001007277 | Hs.643514 |
| 40 | ENOSF1 | Enolase superfamily member 1 | NM_017512 | Hs.369762 |
| 41 | ERCC1 | Excision repair cross-complementing rodent repair deficiency, complementation group 1 (includes overlapping antisense sequence) | NM_202001 NM_001983 | Hs.435981 |
| 42 | ERCC3 | Excision repair cross-complementing rodent repair deficiency, complementation group 3 (xeroderma pigmentosum group B complementing) | NM_000122 | Hs.469872 |
| 43 | ERH | Enhancer of rudimentary homolog (Drosophila) | NM_004450 | Hs.509791 |
| 44 | F13A1 | Coagulation factor XIII, A1 polypeptide | NM_000129 | Hs.335513 |

TABLE 4-continued

FTC marker set FI-1 to FI-147

| Number FI- | marker gene | description of gene | Accession Nr. | UniGeneID |
|---|---|---|---|---|
| 45 | FAM20B | Family with sequence similarity 20, member B | NM_014864 | Hs.5737 |
| 46 | FBP1 | Fructose-1,6-bisphosphatase 1 | NM_000507 | Hs.494496 |
| 47 | FCGR2A | Fc fragment of IgG, low affinity IIa, receptor (CD32) | NM_021642 | Hs.352642 |
| 48 | FGF13 | Fibroblast growth factor 13 | NM_004114 NM_033642 | Hs.6540 |
| 49 | FGFR1OP | FGFR1 oncogene partner | NM_007045 NM_194429 | Hs.487175 |
| 50 | FLNC | Filamin C, gamma (actin binding protein 280) | NM_001458 | Hs.58414 |
| 51 | FMO5 | Flavin containing monooxygenase 5 | NM_001461 | Hs.642706 |
| 52 | FRY | Furry homolog (*Drosophila*) | NM_023037 | Hs.591225 |
| 53 | GADD45G | Growth arrest and DNA-damage-inducible, gamma | NM_006705 | Hs.9701 |
| 54 | GCH1 | GTP cyclohydrolase 1 (dopa-responsive dystonia) | NM_000161 NM_001024024 NM_001024070 NM_001024071 | Hs.86724 |
| 55 | GFRA1 | GDNF family receptor alpha 1 | NM_005264 NM_145793 | Hs.591913 |
| 56 | GLB1 | Galactosidase, beta 1 | NM_001039770 NM_000404 NM_001079811 | Hs.443031 |
| 57 | GOLGA8A | Golgi autoantigen, golgin subfamily a, 8A | NM_181077 NM_001023567 | Hs.182982 |
| 58 | HCLS1 | Hematopoietic cell-specific Lyn substrate 1 | NM_005335 | Hs.14601 |
| 59 | HDGF | Hepatoma-derived growth factor (high-mobility group protein 1-like) | NM_004494 | Hs.506748 |
| 60 | HRC | Histidine rich calcium binding protein | NM_002152 | Hs.436885 |
| 61 | ICMT | Isoprenylcysteine carboxyl methyltransferase | NM_012405 | Hs.562083 |
| 62 | IFNA5 | Interferon, alpha 5 | NM_002169 | Hs.37113 |
| 63 | IGF2BP3 | Insulin-like growth factor 2 mRNA binding protein 3 | NM_006547 | Hs.648088 |
| 64 | IL12A | Interleukin 12A (natural killer cell stimulatory factor 1, cytotoxic lymphocyte maturation factor 1, p35) | NM_000882 | Hs.673 |
| 65 | ITIH2 | Inter-alpha (globulin) inhibitor H2 | NM_002216 | Hs.75285 |
| 66 | ITPKC | Inositol 1,4,5-trisphosphate 3-kinase C | NM_025194 | Hs.515415 |
| 67 | JMJD2A | Jumonji domain containing 2A | NM_014663 | Hs.155983 |
| 68 | KCNJ15 | Potassium inwardly-rectifying channel, subfamily J, member 15 | NM_170736 NM_002243 NM_170737 | Hs.411299 |
| 69 | KCTD12 | Potassium channel tetramerisation domain containing 12 | NM_138444 | Hs.693617 |
| 70 | KIAA0652 | KIAA0652 | NM_014741 | Hs.410092 |
| 71 | KIAA0913 | KIAA0913 | NM_015037 | Hs.65135 |
| 72 | KLKB1 | Kallikrein B, plasma (Fletcher factor) 1 | NM_000892 | Hs.646885 |
| 73 | KRT37 | Keratin 37 | NM_003770 | Hs.673852 |
| 74 | LAMB3 | Laminin, beta 3 | NM_001017402 NM_000228 | Hs.497636 |
| 75 | LPHN3 | Latrophilin 3 | NM_015236 | Hs.694758 Hs.649524 |
| 76 | LRIG1 | Leucine-rich repeats and immuno-globulin-like domains 1 | NM_015541 | Hs.518055 |
| 77 | LSR | Lipolysis stimulated lipoprotein receptor | NM_205834 NM_015925 NM_205835 | Hs.466507 |
| 78 | MANBA | Mannosidase, beta A, lysosomal | NM_005908 | Hs.480415 |
| 79 | MAP7 | Microtubule-associated protein 7 | NM_003980 | Hs.486548 |
| 80 | MAPKAPK5 | Mitogen-activated protein kinase-activated protein kinase 5 | NM_139078 NM_003668 | Hs.413901 |
| 81 | MET | Met proto-oncogene (hepatocyte growth factor receptor) | NM_000245 | Hs.132966 |
| 82 | MMP14 | Matrix metallopeptidase 14 (membrane-inserted) | NM_004995 | Hs.2399 |
| 83 | MX1 | Myxovirus (influenza virus) resistance 1, interferon-inducible protein p78 (mouse) | NM_002462 | Hs.517307 |
| 84 | MYL9 | Myosin, light chain 9, regulatory | NM_006097 NM_181526 | Hs.504687 |
| 85 | MYO9B | Myosin IXB | NM_004145 | Hs.123198 |
| 86 | NCOR1 | Nuclear receptor co-repressor 1 | NM_006311 | Hs.462323 |

TABLE 4-continued

FTC marker set FI-1 to FI-147

| Number FI- | marker gene | description of gene | Accession Nr. | UniGeneID |
|---|---|---|---|---|
| 87 | NDRG4 | NDRG family member 4 | NM_020465<br>NM_022910 | Hs.322430 |
| 88 | NDUFA5 | NADH dehydrogenase (ubiquinone) 1 alpha subcomplex, 5, 13 kDa | NM_005000 | Hs.651219 |
| 89 | NEUROD2 | Neurogenic differentiation 2 | NM_006160 | Hs.322431 |
| 90 | NFKB2 | Nuclear factor of kappa light polypeptide gene enhancer in B-cells 2 (p49/p100) | NM_001077494<br>NM_001077493<br>NM_002502 | Hs.73090 |
| 91 | NME6 | Non-metastatic cells 6, protein expressed in (nucleoside-diphosphate kinase) | NM_005793 | Hs.465558 |
| 92 | NPY1R | Neuropeptide Y receptor Y1 | NM_000909 | Hs.519057 |
| 93 | NUP50 | Nucleoporin 50 kDa | NM_007172<br>NM_153645 | Hs.475103 |
| 94 | PDGFRA | Platelet-derived growth factor receptor, alpha polypeptide | NM_006206 | Hs.74615 |
| 95 | PDHX | Pyruvate dehydrogenase complex, component X | NM_003477 | Hs.502315 |
| 96 | PDLIM1 | PDZ and LIM domain 1 (elfin) | NM_020992 | Hs.368525 |
| 97 | PEX1 | Peroxisome biogenesis factor 1 | NM_000466 | Hs.164682 |
| 98 | PEX13 | Peroxisome biogenesis factor 13 | NM_002618 | Hs.567316 |
| 99 | PIB5PA | Phosphatidylinositol (4, 5) bisphosphate 5-phosphatase, A | NM_014422<br>NM_001002837 | Hs.517549 |
| 100 | PICK1 | Protein interacting with PRKCA 1 | NM_012407<br>NM_001039583<br>NM_001039584 | Hs.180871 |
| 101 | PLEC1 | Plectin 1, intermediate filament binding protein 500 kDa | NM_201380<br>NM_201384<br>NM_000445<br>NM_201379<br>NM_201383<br>NM_201382<br>NM_201381<br>NM_201378 | Hs.434248 |
| 102 | POLE2 | Polymerase (DNA directed), epsilon 2 (p59 subunit) | NM_002692 | Hs.162777 |
| 103 | POLE3 | Polymerase (DNA directed), epsilon 3 (p17 subunit) | NM_017443 | Hs.108112 |
| 104 | PPIF | Peptidylprolyl isomerase F (cyclophilin F) | NM_005729 | Hs.381072 |
| 105 | PPP2R5A | Protein phosphatase 2, regulatory subunit B', alpha isoform | NM_006243 | Hs.497684 |
| 106 | PSCD2 | Pleckstrin homology, Sec7 and coiled-coil domains 2 (cytohesin-2) | NM_017457<br>NM_004228 | Hs.144011 |
| 107 | PSMA5 | Proteasome (prosome, macropain) subunit, alpha type, 5 | NM_002790 | Hs.485246 |
| 108 | PTPN12 | Protein tyrosine phosphatase, non-receptor type 12 | NM_002835 | Hs.61812 |
| 109 | PTPN3 | Protein tyrosine phosphatase, non-receptor type 3 | NM_002829 | Hs.436429 |
| 110 | PTPRCAP | Protein tyrosine phosphatase, receptor type, C-associated protein | NM_005608 | Hs.155975 |
| 111 | QKI | Quaking homolog, KH domain RNA binding (mouse) | NM_206855<br>NM_206854<br>NM_206853<br>NM_006775 | Hs.510324 |
| 112 | RASAL2 | RAS protein activator like 2 | NM_170692<br>NM_004841 | Hs.656823 |
| 113 | RASSF7 | Ras association (RalGDS/AF-6) domain family 7 | NM_003475 | Hs.72925 |
| 114 | RBM10 | RNA binding motif protein 10 | NM_005676<br>NM_152856 | Hs.401509 |
| 115 | RBM38 | RNA binding motif protein 38 | NM_017495<br>NM_183425 | Hs.236361 |
| 116 | RER1 | RER1 retention in endoplasmic reticulum 1 homolog (*S. cerevisiae*) | NM_007033 | Hs.525527 |
| 117 | RGL2 | Ral guanine nucleotide dissociation stimulator-like 2 | NM_004761 | Hs.509622 |
| 118 | RHOG | Ras homolog gene family, member G (rho G) | NM_001665 | Hs.501728 |
| 119 | RNASE1 | Ribonuclease, RNase A family, 1 (pancreatic) | NM_198235<br>NM_198234<br>NM_198232<br>NM_002933 | Hs.78224 |

TABLE 4-continued

FTC marker set FI-1 to FI-147

| Number FI- | marker gene | description of gene | Accession Nr. | UniGeneID |
|---|---|---|---|---|
| 120 | RTN4 | Reticulon 4 | NM_020532<br>NM_207521<br>NM_207520<br>NM_153828<br>NM_007008 | Hs.645283 |
| 121 | RYR2 | Ryanodine receptor 2 (cardiac) | NM_001035 | Hs.109514 |
| 122 | SCC-112 | SCC-112 protein | NM_015200 | Hs.331431 |
| 123 | SDS | Serine dehydratase | NM_006843 | Hs.654416 |
| 124 | SF3B2 | Splicing factor 3b, subunit 2, 145 kDa | NM_006842 | Hs.406423 |
| 125 | SH3PXD2A | SH3 and PX domains 2A | NM_014631 | Hs.594708 |
| 126 | SIX6 | Sine oculis homeobox homolog 6 (*Drosophila*) | NM_007374 | Hs.194756 |
| 127 | SLC10A1 | Solute carrier family 10 (sodium/bile acid cotransporter family), member 1 | NM_003049 | Hs.952 |
| 128 | SLC6A8 | Solute carrier family 6 (neurotransmitter transporter, creatine), member 8 | NM_005629 | Hs.540696 |
| 129 | SMG6 | Smg-6 homolog, nonsense mediated mRNA decay factor (*C. elegans*) | NM_017575 | Hs.448342 |
| 130 | SNRPB2 | Small nuclear ribonucleoprotein polypeptide B" | NM_003092<br>NM_198220 | Hs.280378 |
| 131 | SOX11 | SRY (sex determining region Y)-box 11 | NM_003108 | Hs.432638 |
| 132 | SPI1 | Spleen focus forming virus (SFFV) proviral integration oncogene spi1 | NM_001080547<br>NM_003120 | Hs.502511 |
| 133 | SRGAP3 | SLIT-ROBO Rho GTPase activating protein 3 | NM_014850<br>NM_001033117 | Hs.654743 |
| 134 | STX12 | Syntaxin 12 | NM_177424 | Hs.523855 |
| 135 | SYK | Spleen tyrosine kinase | NM_003177 | Hs.371720 |
| 136 | TAF4 | TAF4 RNA polymerase II, TATA box binding protein (TBP)-associated factor, 135 kDa | NM_003185 | Hs.18857 |
| 137 | TCN2 | Transcobalamin II | NM_000355 | Hs.417948 |
| 138 | TGOLN2 | Trans-golgi network protein 2 | NM_006464 | Hs.593382 |
| 139 | TIA1 | TIA1 cytotoxic granule-associated RNA binding protein | NM_022173<br>NM_022037 | Hs.516075 |
| 140 | TOMM40 | Translocase of outer mitochondrial membrane 40 homolog (yeast) | NM_006114 | Hs.655909 |
| 141 | TXN2 | Thioredoxin 2 | NM_012473 | Hs.211929 |
| 142 | UGCG | UDP-glucose ceramide glucosyltransferase | NM_003358 | Hs.304249 |
| 143 | USP11 | Ubiquitin specific peptidase 11 | NM_004651 | Hs.171501 |
| 144 | VDR | Vitamin D (1,25-dihydroxyvitamin D3) receptor | NM_001017535<br>NM_000376 | Hs.524368 |
| 145 | VEGFC | Vascular endothelial growth factor C | NM_005429 | Hs.435215 |
| 146 | YWHAQ | Tyrosine 3-monooxygenase/tryptophan 5-monooxygenase activation protein, theta polypeptide | NM_006826 | Hs.74405 |
| 147 | ZNF140 | Zinc finger protein 140 | NM_003440 | Hs.181552 |

TABLE 5

PTC marker set PIV-1 to PIV-9

| Number PIV- | marker gene | description of gene | Accession Nr. | UniGeneID |
|---|---|---|---|---|
| 1 | WAS | Wiskott-Aldrich syndrome (eczema-thrombocytopenia) | BC012738 | Hs.2157 |
| 2 | LRP4 | Low density lipoprotein receptor-related protein 4 | BM802977 | Hs.4930 |
| 3 | TFF3 | Trefoil factor 3 (intestinal) | BC017859 | Hs.82961 |
| 4 | ST3GAL6 | ST3 beta-galactoside alpha-2,3-sialyltransferase 6 | BC023312 | Hs.148716 |
| 5 | STK39 | Serine threonine kinase 39 (STE20/SPS1 homolog, yeast) | BM455533 | Hs.276271 |
| 6 | DPP4 | Dipeptidyl-peptidase 4 (CD26, adenosine deaminase complexing protein 2) | BC065265 | Hs.368912 |
| 7 | CHI3L1 | Chitinase 3-like 1 (cartilage glycoprotein-39) | BC038354 | Hs.382202 |

TABLE 5-continued

PTC marker set PIV-1 to PIV-9

| Number PIV- | marker gene | description of gene | Accession Nr. | UniGeneID |
|---|---|---|---|---|
| 8 | FABP4 | Fatty acid binding protein 4, adipocyte | BC003672 | Hs.391561 |
| 9 | LAMB3 | Laminin, beta 3 | BC075838 | Hs.497636 |

TABLE 6

PTC marker set PV-1 to PV-11

| Number PV- | marker gene | description of gene | Accession Nr. | UniGeneID |
|---|---|---|---|---|
| 1 | GPR4 | G protein-coupled receptor 4 | BC067535 | Hs.17170 |
| 2 | STAM2 | Signal transducing adaptor molecule (SH3 domain and ITAM motif) 2 | BC028740 | Hs.17200 |
| 3 | QPCT | Glutaminyl-peptide cyclotransferase (glutaminyl cyclase) | BC047756 | Hs.79033 |
| 4 | CDK7 | Cyclin-dependent kinase 7 (MO15 homolog, *Xenopus laevis*, cdk-activating kinase) | BC000834 | Hs.184298 |
| 5 | SFTPD | Surfactant, pulmonary-associated protein D | BC022318 | Hs.253495 |
| 6 | CYB5R1 | Cytochrome b5 reductase 1 | BC018732 | Hs.334832 |
| 7 | VWF | Von Willebrand factor | BI490763 | Hs.440848 |
| 8 | VWF | Von Willebrand factor | BQ888783 | Hs.440848 |
| 9 | PDHX | Pyruvate dehydrogenase complex, component X | BC010389 | Hs.502315 |
| 10 | HOXA4 | Homeobox A4 | BM996071 | Hs.654466 |
| 11 | HOXA4 | Homeobox A4 | BI521357 | Hs.654466 |

The inventive set can be used to detect cancer or tumor cells, in particular thyroid cancer, and even to distinguish benign thyroid nodules from malignant follicular thyroid carcinoma (FTC) and papillary thyroid carcinoma (PTC). In preferred embodiments the set comprises moieties specific for at least 3 tumor markers selected from the tumor markers PI-1 to PI-33, PII-1 to PII-64, PIII-1 to PIII-70 and PIV-1 to PIV-9, preferably PIV-4 or PIV-5, and PV-1 to PV-11, preferably PV-1, PV-2 and PV-4 to PV-11, in particular from the tumor markers PI-1 to PI-33. These markers are specific for papillary thyroid carcinoma (PTC) and the diagnosed thyroid cancer can be characterized as PTC.

In a similar preferred embodiment the set comprises moieties specific for at least 3 tumor markers selected from the tumor markers FI-1 to FI-147. These markers are specific for follicular thyroid carcinoma (FTC) and the diagnosed thyroid cancer can be characterized as FTC.

Particularly preferred the set comprises a moiety specific for the tumor marker SERPINA1 (Serine (or cysteine) protease inhibitor, Glade A (alpha-1 antiproteinase, antitrypsin), member 1; NM_000295, NM_001002236, NM_001002235), which is a very potent marker for PTC. This marker as single member of the set can distinguish PTC form benign conditions.

Preferably the set comprises at least 5 or at least 10, preferably at least 15, more preferred at least 20, particular preferred at least 25, most preferred at least 30, moieties specific for the tumor markers of table 1 to 6 above. The set may be selected from moieties specific for any at least 3, 4, 5, 6, 7, 8, 9, 10, 11, 12, 13, 14, 15, 16, 17, 18, 19, 20, 25, 30, 33, 35, 40, 45, 50, 55, 60, 64, 65, 70, 75, 80, 85, 90, 95, 100, 110, 120, 130, 140, 145, 147, 150, 160, 170, 180, 190 or 200 of the above tumor markers, e.g. selected from PI-1 to PI-33, PII-1 to PII-64, PIII-1 to PIII-70, FI-1 to FI-147, PIV-1 to PIV-9, preferably PIV-4 or PIV-5, and PV-1 to PV-11, preferably PV-1, PV-2 and PV-4 to PV-11, in particular from any one of PI-1, PI-2, PI-3, PI-4, PI-5, PI-6, PI-7, PI-8, PI-9, PI-10, PI-11, PI-12, PI-13, PI-14, PI-15, PI-16, PI-17, PI-18, PI-19, PI-20, PI-21, PI-22, PI-23, PI-24, PI-25, PI-26, PI-27, PI-28, PI-29, PI-30, PI-31, PI-32, PI-33, PII-1, PII-2, PII-3, PII-4, PII-5, PII-6, PII-7, PII-8, PII-9, PII-10, PII-11, PII-12, PII-13, PII-14, PII-15, PII-16, PII-17, PII-18, PII-19, PII-20, PII-21, PII-22, PII-23, PII-24, PII-25, PII-26, PII-27, PII-28, PII-29, PII-30, PII-31, PII-32, PII-33, PII-34, PII-35, PII-36, PII-37, PII-38, PII-39, PII-40, PII-41, PII-42, PII-43, PII-44, PII-45, PII-46, PII-47, PII-48, PII-49, PII-50, PII-51, PII-52, PII-53, PII-54, PII-55, PII-56, PII-57, PII-58, PII-59, PII-60, PII-61, PII-62, PII-63, PII-64, PIII-1, PIII-2, PIII-3, PIII-4, PIII-5, PIII-6, PIII-7, PIII-8, PIII-9, PIII-10, PIII-11, PIII-12, PIII-13, PIII-14, PIII-15, PIII-16, PIII-17, PIII-18, PIII-19, PIII-20, PIII-21, PIII-22, PIII-23, PIII-24, PIII-25, PIII-26, PIII-27, PIII-28, PIII-29, PIII-30, PIII-31, PIII-32, PIII-33, PIII-34, PIII-35, PIII-36, PIII-37, PIII-38, PIII-39, PIII-40, PIII-41, PIII-42, PIII-43, PIII-44, PIII-45, PIII-46, PIII-47, PIII-48, PIII-49, PIII-50, PIII-51, PIII-52, PIII-53, PIII-54, PIII-55, PIII-56, PIII-57, PIII-58, PIII-59, PIII-60, PIII-61, PIII-62, PIII-63, PIII-64, PIII-65, PIII-66, PIII-67, PIII-68, PIII-69, PIII-70, FI-1, FI-2, FI-3, FI-4, FI-5, FI-6, FI-7, FI-8, FI-9, FI-10, FI-11, FI-12, FI-13, FI-14, FI-15, FI-16, FI-17, FI-18, FI-19, FI-20, FI-21, FI-22, FI-23, FI-24, FI-25, FI-26, FI-27, FI-28, FI-29, FI-30, FI-31, FI-32, FI-33, FI-34, FI-35, FI-36, FI-37, FI-38, FI-39, FI-40, FI-41, FI-42, FI-43, FI-44, FI-45, FI-46, FI-47, FI-48, FI-49, FI-50, FI-51, FI-52, FI-53, FI-54, FI-55, FI-56, FI-57, FI-58, FI-59, FI-60, FI-61, FI-62, FI-63, FI-64, FI-65, FI-66, FI-67, FI-68, FI-69, FI-70, FI-71, FI-72, FI-73, FI-74, FI-75, FI-76, FI-77, FI-78, FI-79, FI-80, FI-81, FI-82, FI-83, FI-84, FI-85, FI-86, FI-87, FI-88, FI-89, FI-90, FI-91, FI-92, FI-93, FI-94, FI-95, FI-96, FI-97, FI-98, FI-99, FI-100, FI-101, FI-102, FI-103, FI-104, FI-105, FI-106, FI-107, FI-108, FI-109, FI-110, FI-111, 112, FI-113, FI-114, FI-115, FI-116, FI-117, FI-118, FI-119, FI-120, FI-121, FI-122, FI-123, FI-124, FI-125, FI-126, FI-127, FI-128, FI-129, FI-130, FI-131, FI-132, FI-133, FI-134, FI-135, FI-136, FI-137, FI-138, FI-139, FI-140, FI-141, FI-142, FI-143, FI-144, FI-145, FI-146, FI-147, PIV-1, PIV-2, PIV-3, PIV-4, PIV-5, PIV-6, PIV-7, PIV-8, PIV-9, PV-1, PV-2, PV-3, PV-4, PV-5, PV-6, PV-7, PV-8, PV-9, PV-10, PV-11. Preferably the set is specific for any complete subset selected from PI, PII, PIII, PIV, PV or FI. However it is also possible to pick any small number from these subsets or combined set since a distinction between benign and malignant states or the diagnosis of cancer can also be performed with acceptable certainty. For example in a preferred embodiment the inventive set comprises at least 5 (or any of the above mentioned numbers) of moieties specific for the tumor markers selected from FI-1 to FI-147. FIGS. 4 and 5 show such diagnostic classification probabilities for PTC and FTC. E.g. a set specific for any number of markers from table 2 (subset PII) specific for 5 markers has only an error margin of 4%, i.e. 96% of all cases would be classified correctly. An error value of 1% (99% certainty) is achieved with at least 20 members. In the case of the FTC specific markers a stable value of 8% errors is achieved with at least 11 different markers selected from the FI subset.

The moieties according to the invention are molecules suitable for specific recognition of the inventive markers. Such molecular recognition can be on the nucleotide, peptide or protein level. Preferably, the moieties are nucleic acids, especially oligonucleotides or primers specific for tumor marker nucleic acids. In another embodiment the moieties are antibodies (monoclonal or polyclonal) or antibody fragments, preferably selected from Fab, Fab' Fab$_2$, F(ab')$_2$ or scFv (single-chain variable fragments), specific for tumor marker proteins. According to the invention it is not of essence which sequence portion of the nucleic acids or which epitopes of the proteins are recognized by the moieties as long as molecular recognition is facilitated. Moieties already known in the art, especially disclosed in the references cited herein, which are all incorporated by reference, are suitable.

In a preferred embodiment the moieties of the set are immobilized on a solid support, preferably in the form of a microarray or nanoarray. The term "microarray", likewise "nanoarray", is used to describe a array of an microscopic arrangement (nanoarray for an array in nanometer scale) or refers to a carrier comprising such an array. Both definitions do not contradict each other and are applicable in the sense of the present invention. Preferably the set is provided on a chip whereon the moieties can be immobilized. Chips may be of any material suitable for the immobilization of biomolecules such as the moieties, including glass, modified glass (aldehyde modified) or metal chips.

According to the present invention a set for the specific use for tumor diagnosis is provided. However, it is also possible to provide larger sets including additional moieties for other purposes, in particular in a microarray set-up, where it is possible to immobilize a multitude of oligonucleotides. However, it is preferred to provide a cost-efficient set including a limited amount of moieties for a single purpose. Therefore, in a preferred embodiment the set comprises at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, especially preferred at least 100%, of the total analyte binding moieties of the set are moieties, which are specific for the tumor markers selected from the group of PI-1 to PI-33, PII-1 to PII-64, PIII-1 to PIII-70, FI-1 to FI-147, PIV-1 to PIV-9, and PV-1 to PV-11 (all markers disclosed in tables 1 to 6, above) or from at least one of the groups of any one of PI-1 to PI-33, PII-1 to PII-64, PIII-1 to PIII-70, FI-1 to FI-147, PIV-1 to PIV-9, PV-1 to PV-11 or any combination thereof. Such preferred combinations are e.g. all markers of the groups PI-1 to PI-33, PII-1 to PII-64, PIII-1 to PIII-70, PIV-1 to PIV-9, and PV-1 to PV-11, being especially suitable for PTC diagnosis. As used herein "analyte binding moieties" refers to all moieties which can be used to specifically detect a marker, in particular a marker gene or gene product, including mRNA or expressed proteins. The genes are preferably genes of a mammal, in particular a human. The moieties are included in this generic term of any "analyte binding moieties" which can have multiple diagnostic targets. E.g., in the embodiment of a microarray the array comprises at least 10% oligonucleotides specific for the inventive markers. Since —according to current technology—detection means for genes on a chip (nucleic acid molecules, such as DNA-ESTs or complementary DNA-ESTs, respectively) allow easier and more robust array design, gene chips using DNA molecules (for detection of expressed mRNA in the sample) is a preferred embodiment of the present invention. Such gene chips also allow detection of a large number of gene products, whereas detection of a large number of proteins using protein chips (e.g. antibody chips) is more difficult. Detection of proteins is usually performed using ELISA techniques (i.e. a microtiter plate-, bead-, or chip-based ELISA) as an embodiment of a protein chip. A protein chip may comprise suitable means for specifically binding the gene products of the gene from the list according to tables 1 to 6, e.g. affinity molecules such as monoclonal or polyclonal antibodies or lectins.

In a further embodiment the set comprises up to 50000 analyte binding moieties, preferably up to 40000, up to 35000, up to 30000, up to 25000, up to 20000, up to 15000, up to 10000, up to 7500, up to 5000, up to 3000, up to 2000, up to 1000, up to 750, up to 500, up to 400, up to 300, or even more preferred up to 200 analyte binding moieties of any kind, such as oligonucleotides specific for any gene or gene product.

In a further aspect the present invention relates to a method for the detection of one or more thyroid cancer markers in a sample comprising using the inventive set and detecting the presence or measuring amount of the occurrence of tumor markers in the sample. The incidence or pattern of the detected markers can specifically identify the presence of these markers which can be relevant for cancer diagnosis or as a reference of healthy samples, or simply a genetic investigation of subjects.

Preferably the sample comprises cells preferably, mammal cells, particular preferred human cells, which can be provided from a biopsy or body fluid. In particular the presence or amount of the tumor markers is detected or measured in these cells after e.g. cell disintegration.

The method may comprise a detection or measurement by RNA-expression analysis, preferably by microarray or quantitative PCR, or protein analysis, preferably by tissue microarray detection, protein microarray detection, mRNA microarray detection, ELISA, multiplex assays, immunohistochemistry, or DNA analysis, comparative genomic hybridization (CGH)-arrays or single nucleotide polymorphism (SNP)-analysis. These methods are known in the art and can be readily used for the method of the present invention, as examples of the vast field of genetic marker analysis.

In another aspect the present invention provides a method for the diagnosis of cancer in a patient, comprising providing a sample, preferably a sample of cells, of the patient, detecting one or more tumor markers by measuring tumor marker signals with the set according to the present invention, comparing the measured signal values of the tumor markers with values of the tumor markers in healthy samples and diagnosing cancer if more than 50%, preferably more than 60%, more preferred more than 70%, most preferred more than 80%, of the values differ compared to the values of the healthy samples by at least the standard deviation, preferably two times the standard deviation, even more preferred three times the standard deviation, of the method of measurement. The differences in genetic expression between samples of diseased subjects and healthy subjects can be of any kind and includes upregulation (e.g. of oncogenes) or downregulation (e.g. of tumor suppressor genes). It is possible that in healthy samples a gene is not expressed whereas expression occurs in diseased samples. The other way around it is also possible that in diseased samples a gene is not expressed whereas expression occurs in healthy samples.

Cancer can also be diagnosed if more than 50%, preferably more than 60%, more preferred more than 70%, most preferred more than 80%, of the values of the sample differ compared to the values of the healthy samples by at least a factor 1.5, at least a factor 2, at least a factor 3 or at least a factor 4. Usually the tumor marker expression products ar up or down regulated by a factor of 2 to 6, but also differences by a factor 60 are possible.

In yet another aspect the invention relates to a method for the identification of disease specific markers, as e.g. given in tables 1 to 6, preferably genes or gene expression patterns, comprising:
  providing gene expression data on multiple potential disease specific genes of at least two different expression datasets,
  determining common genes of the datasets,
  normalising each gene expression dataset, preferably by lowess or quantile normalisation,
  combining the gene expression datasets to a combined dataset, and preferably normalising the combined dataset, and integrating the combined dataset,
  determination of genes of the combined data set by determining its nearest shrunken centroid, which includes the determination of a cross-validated error value of assigning the genes to the disease and minimizing the error value by reducing the number of members of the combined, preferably normalized, data set,
wherein the genes of the reduced data set are the markers specific for the disease. The cross-validation can e.g. the leave-one-out method. Preferably the determination step (the classification step) comprises the determination of a maximized threshold of the difference of the normalized expression value for each gene to the centroid value through the cross-validation. Then the genes with normalized expression values lower than the threshold are removed from the reduced (or shrunken) set and genes with values greater than the threshold to the centroid are specific for the disease. Classification by the shrunken centrois methods are e.g. disclosed by Tibshirani et al. (PNAS USA 99(10):105-114 (2004)), Shen et al. (Bioinformatics 22(22) (2006): 2635-42) and Wang et al. (Bioinformatics 23(8) (2007): 972-9), which disclosures are incorporated herein by reference.

The determination step can be repeated multiple times by leaving out the resulting markers of each previous step. The nearest shrunken centroid method will yield a new result set of further markers which are specific for the disease. Preferably the determination step is repeated 2, 3, 4, 5, 6, 7, 8, 9, 10 or more times. Depending on the size of the combined data set it will give further specific markers. Preferably a cross-validation is performed on each result. The determination can be repeated until the cross-validation indicates an error value of e.g. below 50%, 60%, 70% or 80%. At lower values it can be expected that all markers have been identified.

The initial gene expression data sets are raw expression profiles, e.g. each obtained from a multi genetic microarray analysis. Most of the measured genes are expected not to be involved with the disease and the inventive method is capable to identify characteristic marker genes form at least two, preferably at least three, at least four, at least five, at least six, at least seven or at least eight expression data sets. Therefore the expression data of the initial data sets preferably comprises data of at least two different microarray datasets, in particular with study or platform specific biases. Such biases can occur by using only a specific set up during the measurement of the expression data, e.g. a microarray, which can significantly differ from set ups of other datasets. The present invention has the advantage that during the combination of such sets the problems of such measurement biases are overcome. Furthermore the obtained (initial) gene expression data is raw, unprocessed gene expression data, i.e. no refinement or data conversion was performed prior to the inventive method.

Preferably the disease is a genetic disorder, preferably a disorder with altered gene expression, in particular preferred cancer. Other types of disorders with altered gene expression can be e.g. pathogen infections, in particular viral including retroviral infections, radiation damage and age related disorders.

The step of combining and integrating the combined dataset removed study specific biases. In preferred embodiments this step is performed by stepwise combination of two gene expression datasets per step and integration of the combined dataset, preferably by DWD (Distance Weighted Discrimination). E.g. in the case of 3 data sets at first set 1 is combined with set 2 and the merged set 1+2 is combined with set 3. Integration may e.g. include calculating the normal vector of the combined dataset and subsequently a hyperplane which separates clusters (e.g. of the initial datasets) of data values of the dataset and subtracting the dataset means as in the DWD method. In principle any data integration method which removes biases can be used for the inventive method.

Preferably the at least one, preferably two, three, four, five, six, seven or eight, obtained expression datasets comprise data of at least 10, preferably at least 20, more preferred at least 30, even more preferred at least 40, at least 50, at least 70, at least 100, at least 120, at least 140, at least 160 or at even at least 200 different genes. The inventive method is particularly suitable to filter through large data sets and identify the characteristic markers therein. The obtained set of these markers is also referred to as "classifier".

This method of identifying cancer specific markers and thus moieties, e.g. oligonucleotides or antibodies, specific for cancer can also be used in the above method of diagnosing cancer. I.e. the markers corresponding to the set of moieties used for the diagnostic method are identified (also called "classified") according to the above method which includes the refinement and establishing of centroid values of the measured values of the initial data sets. This pattern can then be used to diagnose cancer if the values of the sample of the patient are closer to the clustered centroid value of the tumor markers. Accordingly a method for the diagnosis of cancer in a patient is provided, comprising providing a sample, preferably a sample of cells, from the patient, detecting one or more tumor markers by measuring tumor marker signals with the set according to the present invention, comparing the measured signal values of the tumor markers with values of the tumor markers in cancer samples by the identification method mentioned above and diagnosing cancer if the nearest shrunken centroid of values of the sample of the patient for at least 50%, preferably at least 60%, more preferred at least 70% or even at least 80%, most preferred 90%, markers of the set is within the standard deviation, preferably two times the standard deviation, even more preferred three times the standard deviation, of the method of measurement to the nearest shrunken centroid of the tumor markers identified with the cancer samples.

The present invention is further illustrated by the following figures and examples without being specifically restricted thereto. All references cited herein are incorporated by reference.

DETAILED DESCRIPTION

EXAMPLES

Example 1

Datasets

Datasets were downloaded either from websites or from public repositories (GEO, ArrayExpress). Table 7 shows a summary of the datasets used in this study (He et al, PNAS USA 102(52): 19075-80 (2005); Huang et al. PNAS USA 98(26): 15044-49 (2001); Jarzab Cancer Res 65(4): 1587-97 (2005); Lacroix Am J Pathol 167(1): 223-231 (2005); J Clin Endocrinol Metab 90(5): 2512-21 (2005)). Here, three different categories of non-cancer tissues are used: contralateral (c.lat) for healthy surrounding tissue paired with a tumor sample, other disease (o.d.) for thyroid tissue operated for other disease and SN (Struma nodosa) for benign thyroid nodules. For all subsequent analysis these were combined as healthy.

TABLE 7

Microarray Data used for Meta Analysis

|  | Published | FTA | FTC | PTC | SN | o.d. | c.lat | Platform |
|---|---|---|---|---|---|---|---|---|
| He | PNAS 2005 | 0 | 0 | 9 | 0 | 0 | 9 | Affy U133plus |
| Huang | PNAS 2001 | 0 | 0 | 8 | 8 | 0 | 0 | Affy U133A |
| Jarzab | Cancer Res 2005 | 0 | 0 | 23 | 0 | 11 | 17 | Affy U133A |
| Lacroix | Am J Path 2005 | 4 | 8 | 0 | 11 | 0 | 0 | Agilent Custom |
| Reyes | not published? | 0 | 0 | 7 | 0 | 0 | 7 | Affy U133A |
| Weber | J Clin Endocr Metabol 2005 | 12 | 12 | 0 | 0 | 0 | 0 | Affy U95A |

Example 2

Finding the Gene Overlap

The first step in any MetaAnalysis of microarray data is to find the set of genes which is shared by all microarray platforms used in the analysis. Traditionally, overlap is assessed by finding common UniGene identifiers. This, however, disregards all possible splice variations in the genes under investigation. For example, if a gene had 2 splice variants, one of which was differentially expressed in the experiment and the other not and if one platform would contain an oligo specific only to the differentially expressed variant and the other platform only an oligo to the other variant, then a matching based on UniGene would merge probes which measure different things.

To overcome this problem, the approach adopted here merges only probes which annotate to the same set of RefSeq identifiers. To this end all matching RefSeqs were downloaded for each probe(set), either via the Bioconductor annotation packages (hgu133a, hgu95a and hgu133plus2; available at the Bioconductor web page or by a BLAST search of the sequences at NCBI Database. Then, for each probe the RefSeqs were sorted and concatenated. This is the most accurate representation of the entity measured on the array. The median value was used, if one set of RefSeqs was represented by multiple probes on the array. 5707 different sets of RefSeqs were present on all arrays.

Example 3

Preprocessing and Data Integration

Figure 1:
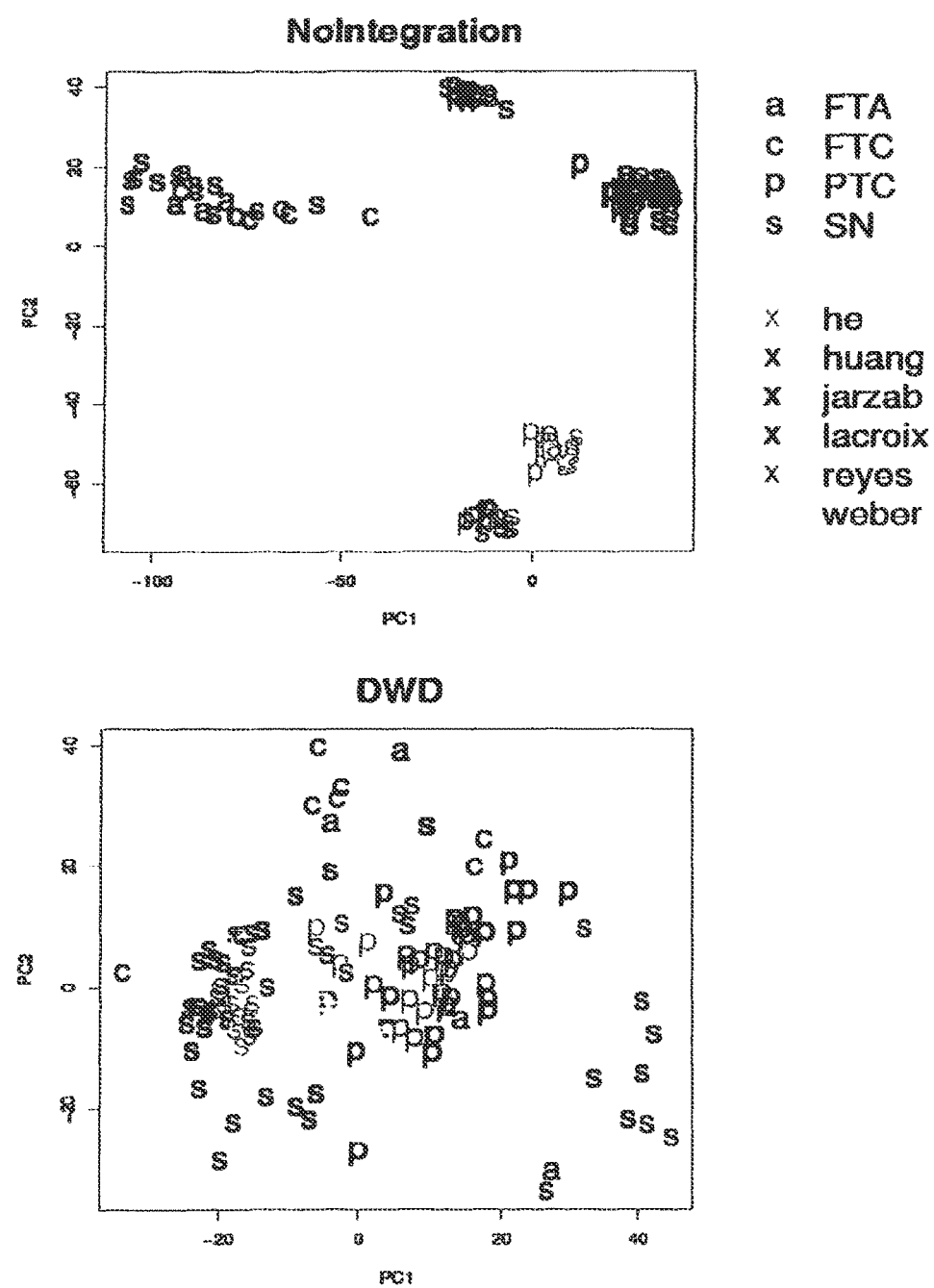
FIG. 1: The first two principal components before and after DWD—integration. Datasets are coded by colour and tumor entities are coded by letters according to the legend.

First each dataset was background-corrected and normalised separately, as recommended for each platform (lowess for dual color and quantile normalisation for single color experiments) (Bolstad et al. Bioinformatics 19(2): 185-193 (2003); Smyth et al. Methods 31(4): 265-273 (2003)), then they were merged and quantile normalised collectively. Despite all preprocessing, it has been shown that data generated on different microarray platforms or on different generations of the same platform may not be comparable due to platform specific biases (Eszlinger et al. Clin Endocrinol Metab 91(5): 1934-1942 (2006)). This is also evident from principal component analysis of the merged data as shown in FIG. 1. In order to correct for these biases, methods have been developed for integration of microarray data. One of these methods is Distance Weighted Discrimination (DWD) which is described in detail elsewhere (Benito et al. Bioinformatics 20(1): 105-114 (2004)). Briefly, DWD projects data points onto the normal vector of a class (dataset)—separating hyperplane as calculated by a modified Support Vector Machine (SVM) and subtracts the class (dataset) means. Therefore, for a multiclass problem (more than 2 datasets to merge), the datasets need to be merged sequentially. For 6 datasets this leads to 720 different possibilities for merging, not including tree structured approaches, e.g instead of (((1+2)+3)+4), consider ((1+2)+(3+4)). The merging orders applied here were chosen on the general idea that similar and larger datasets should be merged first and more disparate ones later. It is also worth noting, that adding a sample to a DWD merged dataset will change the whole dataset just like adding a new number to a vector of numbers will change its mean.

Figure 2:
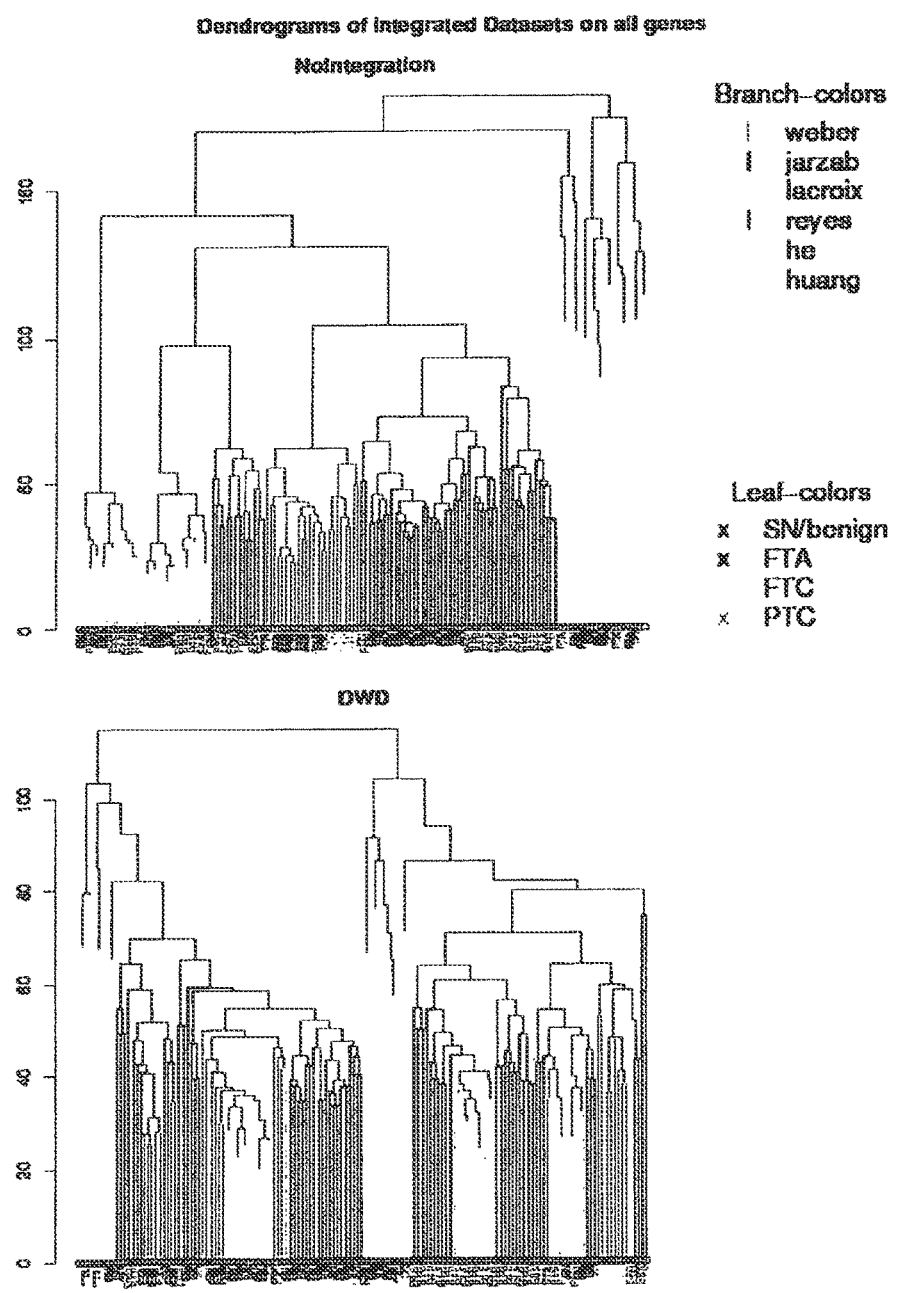
FIG. 2: Dendrogram of the DWD integrated data on all genes. The colors of branches of the dendrogram indicate the dataset of the corresponding sample, the color of the leaf-label indicates the tumor entity.

Data Integration by DWD is illustrated in FIG. 1 which shows the effect of the data integration method on the first two principal components. In this analysis, DWD was able to remove the separation between the datasets as indicated by the PC-plots and by the mixing of the branches in the dendrogram (see FIG. 2). However, even in the DWD-integrated dataset the Lacroix data still partly separates from the other data. Most likely this is due to the platform; the lacroix-data is the only data from a non-Affymetrix platform. FIG. 2 shows dendrograms of the respective integrated datasets. Also, DWD integration does not seem to hamper the discrimination between the tumor entities (see table 8 below).

Example 4

Classification

For probe selection, classification and cross-validation a nearest shrunken centroid method was chosen (Tibshirani et al. PNAS USA 99(10):105-114 (2004)) (implemented in the Bioconductor package pamr). It was chosen for several reasons: it allows multiclass classification and it runs features selection, classification and cross-validation in one go. Briefly, it calculates several different possible classifiers using different shrinkage thresholds (i.e. different number of genes) and finds the best threshold from crossvalidation. The classifier was picked with the smallest number of genes (largest threshold), if more than one threshold yielded the same crossvalidation results.

Example 5

Papillary Thyroid Carcinoma (PTC)

First, and as a quality measure for each study, each dataset was taken separately (before DWD-integration) and a pamr classification and leave-one-out cross-validation (loocv) was performed. The results of the cross-validation are near perfect with single samples classifying wrongly. However, with the exception of the classifier from the He dataset, none of these classifiers can be applied to any of the other dataset. Classification results are rarely ever higher than expected by chance. If, however, one uses the DWD-integrated data (below), the classifiers already fit much better (see table 8).

TABLE 8

Classification results when applying classifiers from one study on another study. Before data integration (left) and after DWD integration (right)

| test train | he | huang | jarzab | reyes | test train | he | huang | jarzab | reyes |
|---|---|---|---|---|---|---|---|---|---|
| he | 1.00 | 1.00 | 0.98 | 1.00 | he | 1.00 | 1.00 | 0.96 | 1.00 |
| huang | 0.50 | 1.00 | 0.55 | 0.50 | huang | 0.50 | 1.00 | 0.90 | 0.71 |
| jarzab | 0.50 | 0.81 | 1.00 | 0.57 | jarzab | 0.89 | 1.00 | 1.00 | 1.00 |
| reyes | 0.78 | 0.50 | 0.92 | 1.00 | reyes | 0.89 | 0.88 | 0.90 | 1.00 |

Figure 3:
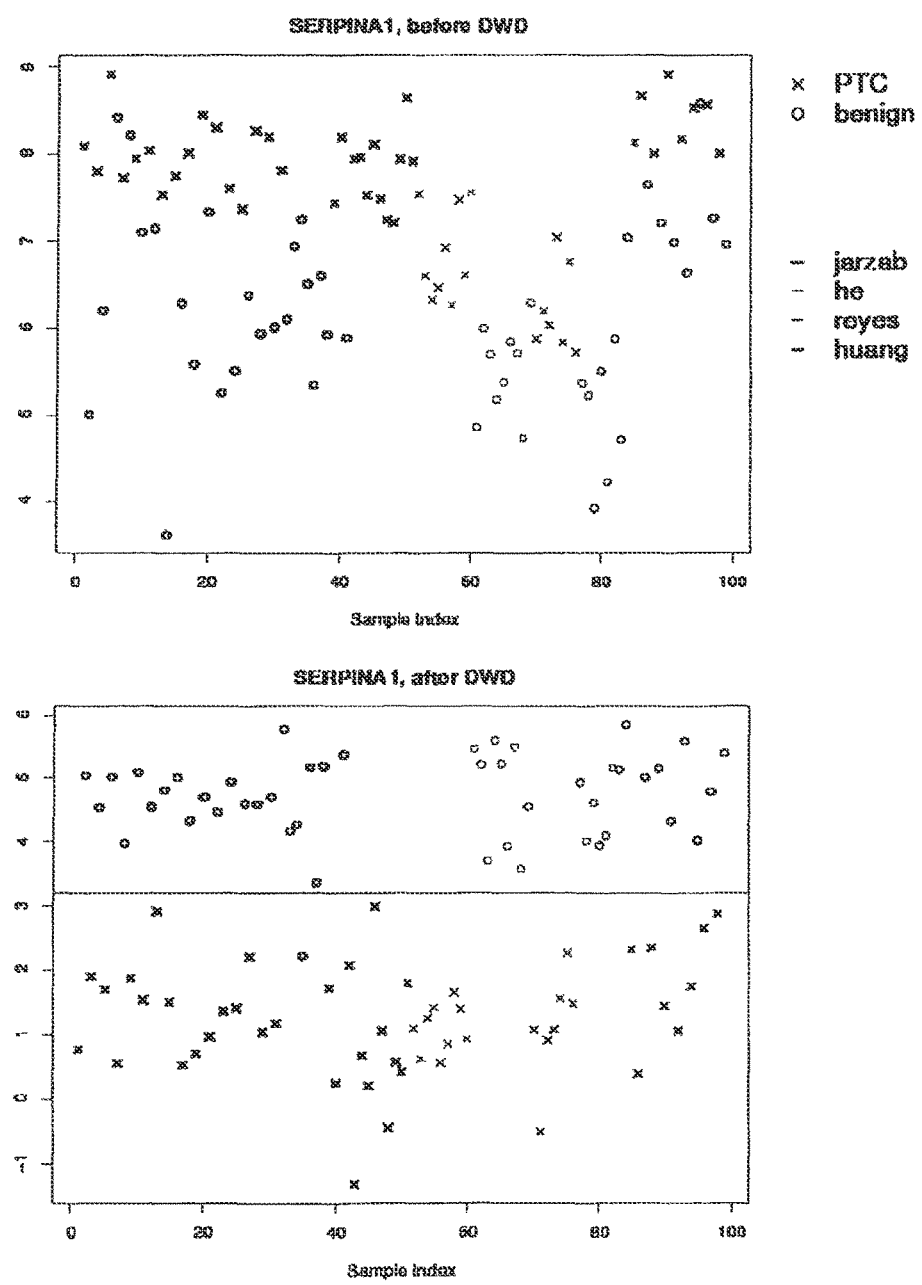
FIG. 3: Discrimination between papillary carcinoma and benign nodules across four different datasets by only one gene (SERPINA1)
Figure 4:
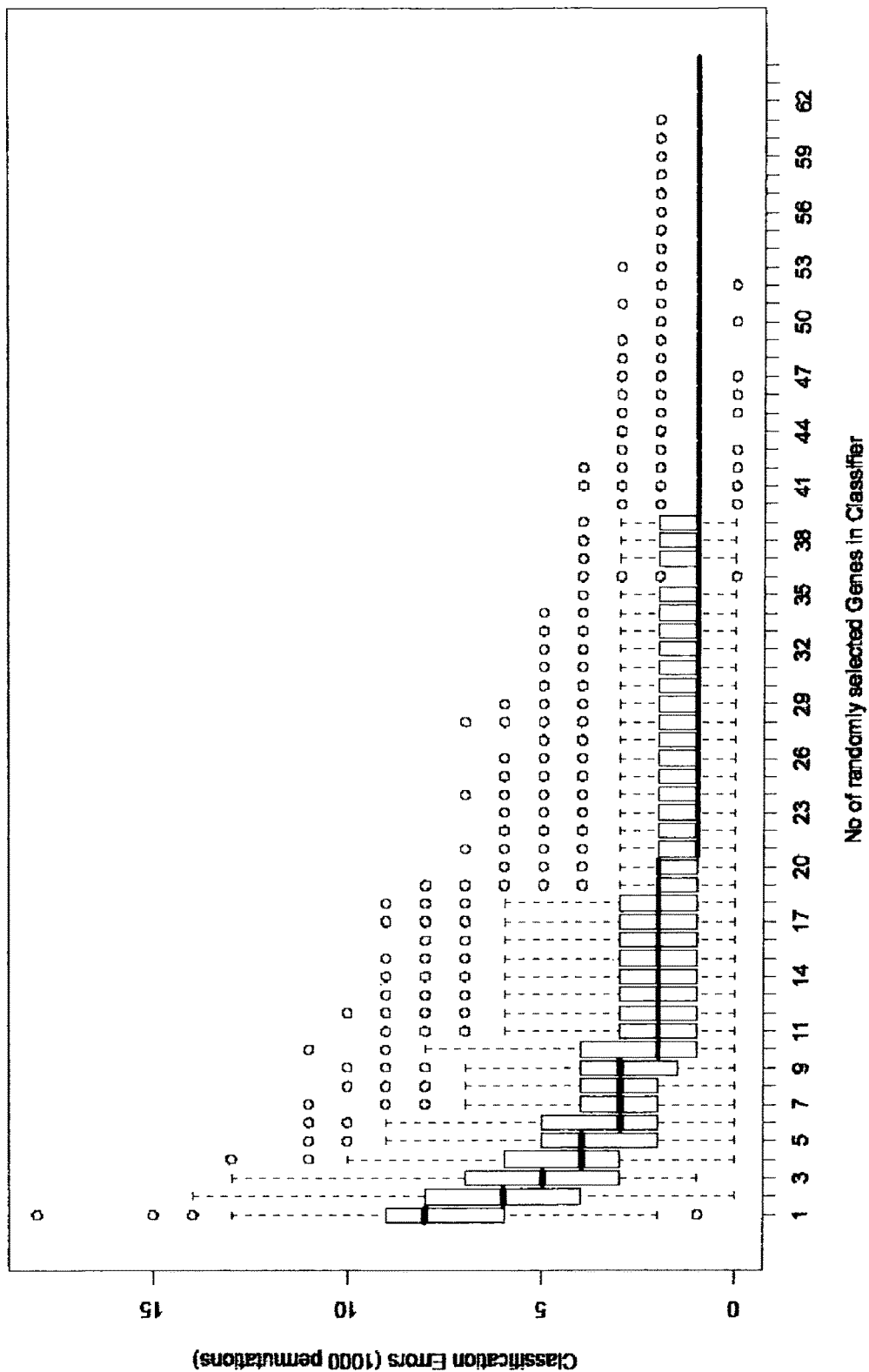
FIG. 4 shows a graph of the average error probability during PTC classification of seduced sets (classifier) of markers from table 2.
Figure 5:
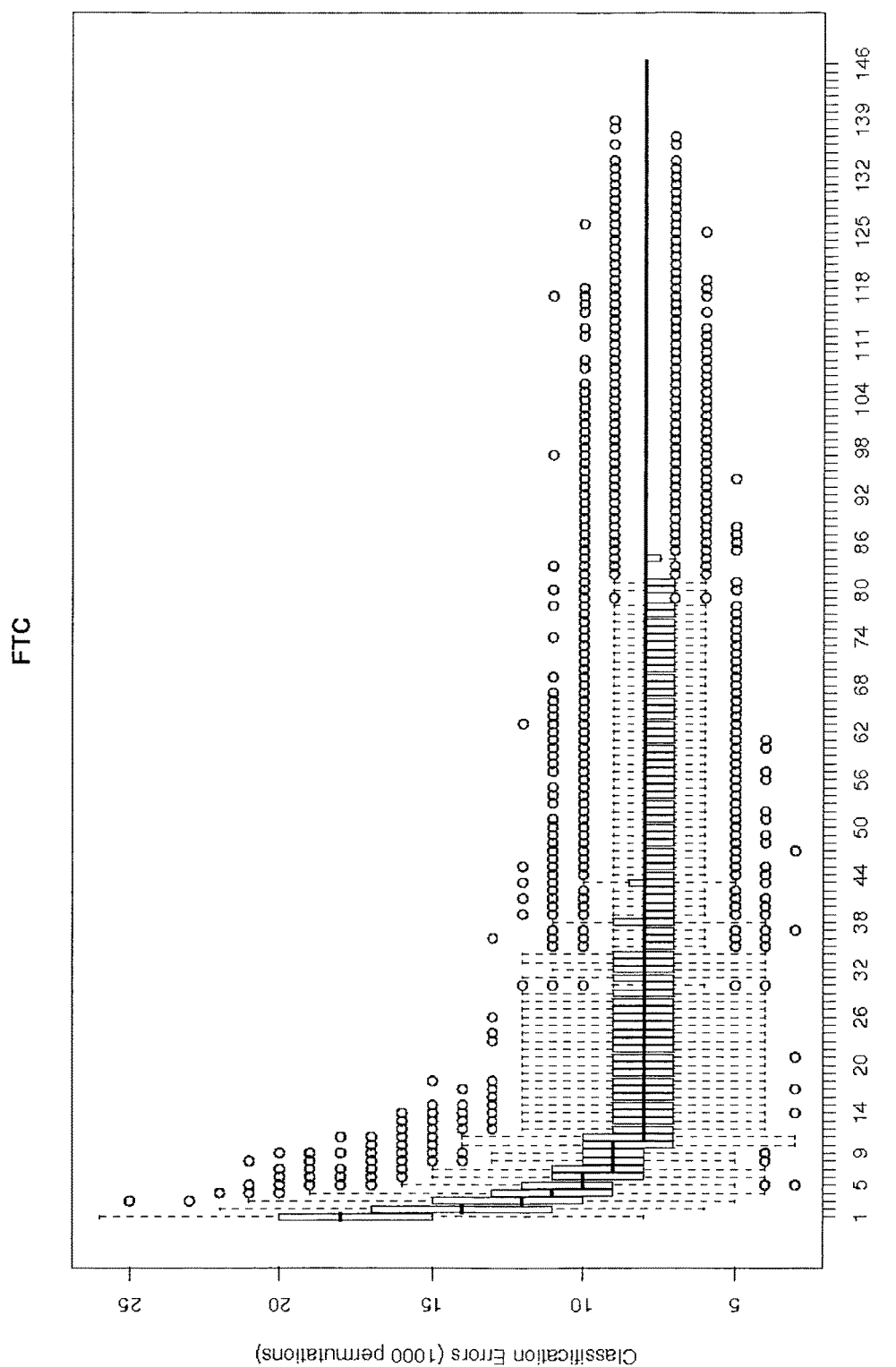
FIG. 5 shows a graph of the average error probability during FTC classification of seduced sets (classifier) of markers from table 4.

Then a pamr-classifier was built for the complete DWD-integrated dataset and validated in a leave-one-out cross validation. This identified a one (!) gene classifier, which classifies 99% of samples correctly in loocv. The discriminative gene is SERPINA1. FIG. 3 shows the discrimination of PTC vs SN before and after DWD. One could add up to 422 genes to the classifier and still yield 99% accuracy (from loocv). If one removes the SERPINA1-probe from the analysis, one can build again a classifier (subsequently denominated classifier) with 99% accuracy in loocv, this time using a 9-gene signature (see Table 3). Removing these 9 genes yields another 9-gene classifier with a similar performance (99% accuracy), and further an 11-gene classifier with 99% accuracy. Such further classifiers are e.g. given in tables 1 to 3, 5 and 6 (above) for PTC.

However, similar results are obtained doing the same analysis on the non-integrated data. Taking into account the results of PCA (FIG. 1), where it was obvious that the variance explained by the different datasets is much larger than the variance explained by tumor entity, one could imagine that the bias introduced by the datasets may help (or hamper) classification. Therefore a study-crossvalidation was performed, whereby sequentially one study was taken out from the dataset, a was classifier built from the remaining samples and tested on the eliminated dataset. On the DWD-integrated data, the accuracy of prediction was 100, 100, 98 and 100% leaving out He, Huang, Jarzab and Reyes from the classifier, respectively. For the non-integrated data, the results were similar (100, 100, 94 and 100%).

TABLE 9

Genes in classifier2 (after leaving out SERPINA1)

| Symbol | Title | Cluster | Accession |
|---|---|---|---|
| WAS | Wiskott-Aldrich syndrome (eczema-thrombocytopenia) | Hs.2157 | BC012738 |
| LRP4 | Low density lipoprotein receptor-related protein 4 | Hs.4930 | BM802977 |
| TFF3 | Trefoil factor 3 (intestinal) | Hs.82961 | BC017859 |
| ST3GAL6 | ST3 beta-galactoside alpha-2,3-sialyltransferase 6 | Hs.148716 | BC023312 |
| STK39 | Serine threonine kinase 39 (STE20/SPS1 homolog, yeast) | Hs.276271 | BM455533 |
| DPP4 | Dipeptidyl-peptidase 4 (CD26, adenosine deaminase complexing protein 2) | Hs.368912 | BC065265 |
| CHI3L1 | Chitinase 3-like 1 (cartilage glycoprotein-39) | Hs.382202 | BC038354 |
| FABP4 | Fatty acid binding protein 4, adipocyte | Hs.391561 | BC003672 |
| LAMB3 | Laminin, beta 3 | Hs.497636 | BC075838 |

Example 6

Follicular Carcinoma

A similar analysis was also performed for the FTC data, but cross-validation was hampered, due to the very limited availability of data. Again, a classifier was built for each dataset (Lacroix and Weber). They achieved a loocv-accuracy of 96% (Weber) and 100% (Lacroix) on 25 and 3997 genes. The number of genes in the Lacroix-data already suggests overfitting, which was confirmed by cross-classification with the other dataset (25 and 35% accuracy, respectively). Also, the gene-overlap between the two classifiers is low (between 0 and 10% depending on the threshold). If, however the 2 datasets are combined using DWD, a 147-gene classifier (table 4 above) could be built which was able to correctly identify samples (with a 92% accuracy).

Example 7

Discussion

The present invention represents the largest cohort of thyroid carcinoma microarray data analysed to date. It makes use of the novel combinatory method using the latest algorithms for microarray data integration and classification. Nevertheless, meta-analysis of microarray data still poses a challenge, mainly because single microarray investigations are aimed at at least partly different questions and hence use different experimental designs. Moreover, the number of thyroid tumor microarray data available to date is still comparably low (compared to breast cancer, e.g.). Therefore, when doing meta-analysis, one is forced to use all data available, even if the patient cohorts represent a rather heterogeneous and potentially biased population. More specifically, it is difficult to obtain a homogenous collection of control material (from healthy patients). These are usually taken from patients who were operated for other thyroid disease which is in turn very likely to cause a change in gene expression as measured on microarrays. The generation of homogeneous patient cohorts is further hampered by limited availability of patient data like age, gender, genetic background, etc.

When doing meta-analysis of microarray data, many researchers have based their approach on comparing gene lists from published studies (Griffith et al, cited above). This is very useful, as one can include all studies in the analysis and is not limited to the studies where raw data is available. However, the studies generally follow very different analysis strategies, some more rigorous than others. It is not under the control of the meta-analyst how the authors arrived at the gene lists. Therefore these analyses may be biased.

Regarding data integration, according to the original DWD paper, DWD performs best when at least 25-30 samples per dataset are present. In the present study, 4 out of 6 datasets contained less than 20 samples. Still DWD performed comparably well for removing platform biases (see Table 8).

DWD greatly improved the results of PCA (FIG. 1), hierarchical clustering (FIG. 2) and the classification accuracy when applying a classifier from one study to another study (Table 8). In this light it was surprising to see that the non-integrated data performed equally well in the study cross-validation compared to the DWD-integrated data. One explanation for this is that any study-specific bias will become less important the more studies are being evaluated. Given that the study bias affects some genes more than others, the more affected genes will be less likely to survive the pamr-thresholding due to the variance introduced by the study-bias. However, as shown above, there is a large abundance of genes discriminating PTC and benign nodules. As long as one (or a few) of those genes is not affected by the study bias, it (they) will survive thresholding and discrimination between tumor entities will still be possible.

There is an apparent discrepancy when one looks at FIG. 3: Before DWD, the PTC samples have a higher SERPINA1 expression while after DWD it is the other way round. However, as noted in the Materials and Methods section, DWD subtracts the class means from each sample. This simply means that before DWD the study bias for SERPINA1 is higher than the difference in expression between the tumor classes. This also explains, why in the not-integrated data SERPINA1 is not a well working classifier.

A recent Meta-Analysis and Meta-Review by Griffith et. al. (cited above) has summarised genes with a diagnostic potential in the context of thyroid disease. They published lists of genes which appeared in more than one high-throughput study (Microarray, SAGE) analysing thyroid disease and applied a ranking system. In their analysis SERPINA1 scored the third highest, and TFF3, which is part of classifier2 (when leaving out SERPINA1), scored second. Four out of nine genes from classifier2 appeared in the list from Griffith et. al. (LRP4, TFF3, DPP4 and FABP4).

Most of these lists were generated from microarray analysis. However, even when comparing the genes in the classifiers to gene lists generated with independent technologies, like cDNA library generation, there is substantial overlap. SERPINA1 appears in their lists as well as four out of the nine genes from classifier2 (TFF3, DPP4, CHI3L1 and LAMB3).

For the case of follicular thyroid disease, building a robust classifier is much more difficult. This is mainly down to the limited availability of data. Also, the two datasets were very different in terms of the platforms used; while all other datasets were generated on Affymetrix GeneChips arrays of different generations, the Lacroix data was generated on a custom Agilent platform. Nevertheless the classifier (set) of table 4 was able to identify most samples correctly in loocv.

The power of the meta analysis approach adopted here is demonstrated by a 99% loocv-accuracy (97.9% weighted average accuracy in the study cross-validation) for the distinction between papillary thyroid carcinoma and benign nodules. This has been achieved on the largest and most diverse dataset so far (99 samples from 4 different studies).

One sample was classified wrongly, and although it is not possible to correctly map the samples from this analysis to the original analysis, the misclassified sample is from the same group (PTC, validation group) as the sample which was wrongly classified in the original analysis. According to Jarzab et. al. the sample was an outlier because it contained only ≈20% tumor cells.

What is claimed is:

1. A set of moieties comprising moieties specific for at least 3 tumor markers, wherein the three tumor markers are selected from the group consisting of SCEL and CD36 and either MDK or DPP6, wherein the moieties are immobilized on a solid support, wherein the moieties are oligonucleotides specific for nucleic acids of tumor marker genes, and wherein the set of moieties comprises 1000 moieties or less.

2. The set of claim 1, wherein at least one of the three tumor markers is MDK.

3. The set of claim 1, wherein at least one of the three tumor markers is DPP6.

4. The set of claim 1, further comprising at least a fourth moiety specific for a tumor marker selected from the markers of tables 1 to 6.

5. The set for claim 1, further comprising at least 10 moieties specific for the tumor markers selected from the markers of tables 1 to 6.

6. The set of claim 1, wherein the solid support is a microarray.

7. The set of claim 1, wherein at least 10% of all moieties immobilized on the solid support are oligonucleotides specific for nucleic acids of one or more tumor marker genes selected from BBS9, C13orf1, CBFA2T3, CDT1, CRK, CTPS, DAPK2, EIF5, EREG, GK, GPATCH8, HDGF, IRF2BP1, KRT83, MYOD1, NME6, POLE3, PPP1R13B, PRPH2, RASSF7, ROCK2, RTN1, S100B, SLIT2, SNRPB2, SPAG7, STAU1, SUPT5H, TBX10, TLK1, TM4SF4, TXN, UFD1L, ADH1B, AGR2, AGTR1, ALDH1A1, ALDH1A3, AMIGO2, ATP2C2, BID, C7orf24, CA4, CCL21, CD55, CDH16, CDH3, CFI, CHI3L1, CHST2, CITED2, CLCNKB, COMP, CTSH, DIO2, DIRAS3, DUSP4, DUSP5, EDN3, ENTPD1, FHL1, GDF15, GPM6A, HBA1, IRS1, KCNJ2, KCNN4, KLK10, LAMB3, LCN2, LMOD1, MATN2, MPPED2, MVP, NELL2, NFE2L3, NPC2, NRCAM, NRIP1, PAPSS2, PDLIM4, PDZK1IP1, PIP3-E, PLAU, PRSS2, PRSS23, RAP1GAP, S100A11, SFTPB, SLPI, SOD3, SPINT1, SYNE1, TACSTD2, UPP1, WASF3, APOE, ATIC, BASP1, C9orf61, CCL13, CDH6, CFB, CFD, CLDN10, COL11A1, COL13A1, CORO2B, CRLF1, CXorf6, DDB2, DPP6, ECM1, EFEMP1, ESRRG, ETHE1, FAS, FMOD, GABBR2, GALE, GATM, GDF10, GHR, GPC3, ICAM1, ID3, IER2, IGFBP6, IQGAP2, ITGA2, ITGA3, ITM2A, KIAA0746, LRIG1, LRP2, LY6E, MAPK13, MDK, MLLT11, MMRN1, MTMR11, MXRA8, NAB2, NMU, OCA2, PDE5A, PLAG1, PLP2, PLXNC1, PRKCQ, PRUNE, RAB27A, RYR2, SELENBP1, SORBS2, STMN2, TBC1D4, TNC, TPD52L1, TSC22D1, TTC30A, VLDLR, WFS1, AATF, ACOX3, AHDC1, ALAS2, ALKBH1, ANGPTL2, AP2A2, APOBEC3G, APRIN, ARNT, AZGP1, BAT2D1, BATF, BPHL, C14orf1, C2orf3, CBFB, CBR3, CBX5, CCNE2, CD46, CHPF, CHST3, CLCN2, CLCN4, CLIC5, CNOT2, COPS6, CPZ, CSK, CTDP1, DDEF2, DKFZP586H2123, DLG2, DPAGT1, DSCR1, DUSP8, EI24, ENOSF1, ERCC1, ERCC3, ERH, F13A1, FAM20B, FBP1, FCGR2A, FGF13, FGFR1OP, FLNC, FMO5, FRY, GADD45G, GCH1, GFRA1, GLB1, GOLGA8A, HCLS1, HRC, ICMT, IFNA5, IGF2BP3, IL12A, ITIH2, ITPKC, JMJD2A, KCNJ15, KCTD12, KIAA0652, KIAA0913, KLKB1, KRT37, LPHN3, LSR, MANBA, MAP7, MAPKAPK5, MET, MMP14, MX1, MYL9, MYO9B, NCOR1, NDRG4, NDUFA5, NEUROD2, NFKB2, NPY1R, NUP50, PDGFRA, PDHX, PDLIM1, PEX1, PEX13, PIB5PA, PICK1, PLEC1, POLE2, PPIF, PPP2R5A, PSCD2, PSMA5, PTPN12, PTPN3, PTPRCAP, QKI, RASAL2, RBM10, RBM38, RER1, RGL2, RHOG, RNASE1, RTN4, SCC-112, SDS, SF3B2, SH3PXD2A, SIX6, SLC10A1, SLC6A8, SMG6, SOX11, SPI1, SRGAP3, STX12, SYK, TAF4, TCN2, TGOLN2, TIA1, TOMM40, TXN2, UGCG, USP11, VDR, VEGFC, YWHAQ, ZNF140, WAS, LRP4, TFF3, ST3GAL6, STK39, DPP4, FABP4, GPR4, STAM2, QPCT, CDK7, SFTPD, CYB5R1, VWF, and HOXA4.

8. The set of claim 1, wherein the set comprises 700 moieties or less.

9. The set of claim 8, wherein the set comprises 500 moieties or less.

10. The set of claim 8, wherein the set comprises 300 moieties or less.

* * * * *